United States Patent
Seto et al.

(10) Patent No.: US 6,995,153 B2
(45) Date of Patent: Feb. 7, 2006

(54) FUSED BICYCLIC PYRIMIDINE DERIVATIVES

(75) Inventors: Shigeki Seto, Tochigi (JP); Asao Tanioka, Saitama (JP); Makoto Ikeda, Ibaraki (JP); Shigeru Izawa, Tochigi (JP)

(73) Assignee: Kyorin Pharmaceutical. Co., Ltd., Tokyo (JP)

( * ) Notice: Subject to any disclaimer, the term of this patent is extended or adjusted under 35 U.S.C. 154(b) by 0 days.

(21) Appl. No.: 10/501,551

(22) PCT Filed: Jan. 15, 2003

(86) PCT No.: PCT/JP03/00263

§ 371 (c)(1),
(2), (4) Date: Jul. 16, 2004

(87) PCT Pub. No.: WO03/062245

PCT Pub. Date: Jul. 31, 2003

(65) Prior Publication Data

US 2005/0085469 A1    Apr. 21, 2005

(30) Foreign Application Priority Data

Jan. 18, 2002 (JP) .............................. 2002-009373

(51) Int. Cl.
  C07D 498/04    (2006.01)
  A61K 31/519   (2006.01)
  A61K 31/553   (2006.01)
  A61K 31/5377  (2006.01)
  A61P 19/02    (2006.01)

(52) U.S. Cl. ............. 514/211.05; 514/218; 514/234.2; 514/254.11; 514/260.1; 540/455; 540/490

(58) Field of Classification Search ............... 540/455, 540/490; 514/211.05, 218, 234.2, 254.11, 514/260.1
See application file for complete search history.

(56) References Cited

U.S. PATENT DOCUMENTS 6,147,071 A    11/2000  Natsugari et al.

FOREIGN PATENT DOCUMENTS

EP    652218    5/1995
WO    97/24356   7/1997

*Primary Examiner*—Bruck Kifle
(74) *Attorney, Agent, or Firm*—Wenderoth, Lind & Ponack, L.L.P.

(57) ABSTRACT

A novel fused bicyclic pyrimidine derivative or a salt thereof that acts as a tachykinin receptor antagonist and, in particular, as an NK1 receptor antagonist is represented by the following general formula (1):

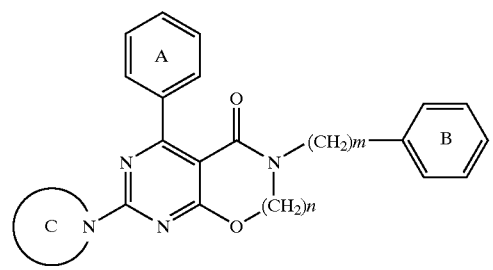

wherein the rings A and B are each a benzene ring having 1 to 3 substituents (any adjacent two of which may be bound to one another to form a ring); the ring C is a nitrogen-containing ring; m is 1 or 2; and n is 2 or 3.

15 Claims, No Drawings

FUSED BICYCLIC PYRIMIDINE DERIVATIVES

TECHNICAL FIELD

The present invention relates to novel fused bicyclic pyrimidine derivatives and pharmaceutically acceptable salts thereof that act as tachykinin receptor antagonists. The present invention also relates to medical applications of such compounds.

TECHNICAL BACKGROUND

'Tachykinin' is a collective term for such neuropeptides as substance P, neurokinin A, and neurokinin B. These tachykinins are known to exhibit various physiological activities by binding to corresponding receptors in a human body (neurokinin 1 (NK1), neurokinin 2 (NK2), and neurokinin 3 (NK3), respectively). Of different tachykinins, substance P, aside from its role as a neurotransmitter in primary sensory neurons in central and peripheral nervous systems, brings about various physiological effects, such as diuresis, excitation of neurons, increased blood vessel permeability, blood vessel dilation, contraction of smooth muscles, and immune activities. Substance P is also believed to play significant roles in the onset of various pathological conditions such as pollakiuria, incontinence, vomiting, inflammation, allergies, respiratory tract disorders, pains, and central nervous system disorders. Thus, a need exists for the development of a compound that acts as a tachykinin receptor antagonist and, in particular, as an NK1 receptor antagonist and is thus suitable for use as an effective prophylactic or therapeutic agent against various pathological conditions such as those mentioned above. It is also desirable that such a compound offer high safety, persistence of efficacy, and other advantageous characteristics.

At present, the following compounds are known as NK1 receptor antagonists and are described in the following publications:

(1) European Patent Application Publication No. EP-A-429366 describes compounds such as the one represented by the following formula:

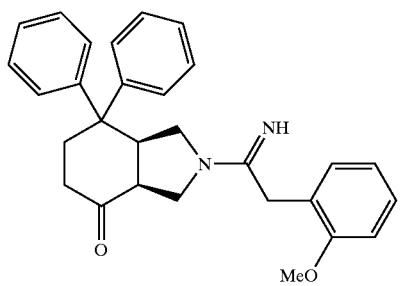

(2) PCT pamphlet (International Patent Publication) No. WO91/09844 describes compounds such as the one represented by the following formula:

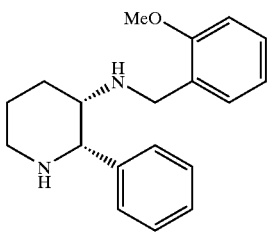

(3) European Patent Application Publication No. EP-A-532456 describes compounds such as the one represented by the following formula:

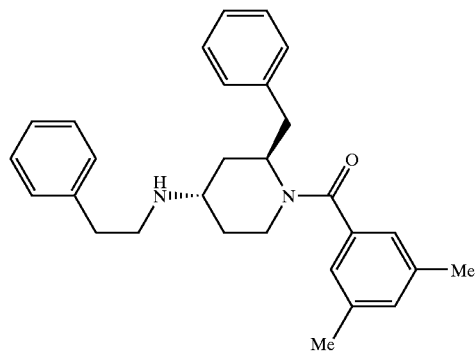

(4) European Patent Application Publication No. EP-A-522808 describes compounds such as the one represented by the following formula:

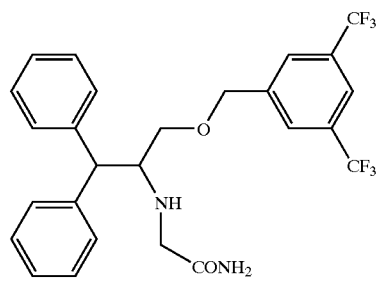

(5) PCT pamphlet (International Patent Publication) No. WO93/01169 describes compounds such as the one represented by the following formula:

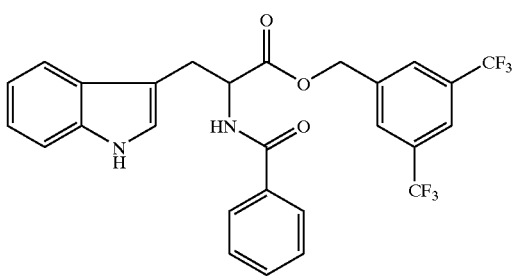

(6) Japanese Patent Laid-Open Publication No. Hei 8-67678 describes a compound represented by the following formula and salts thereof:

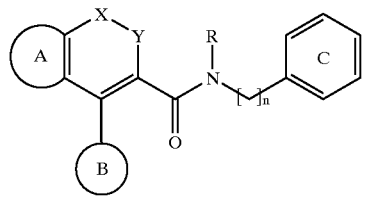

wherein the rings A and B are each a homocyclic or heterocyclic ring with at least one of the rings A and B being a heterocyclic ring; the ring C is a benzene ring; R is H or a hydrocarbon residue; one of X and Y is —$NR^1$— (where $R^1$ is H or a hydrocarbon residue) or —O— and the other is —CO— or —CS—, or one of X and Y is —N= and the other is =$CR^2$— (where $R^2$ is H, a halogen, a hydrocarbon residue, an amino, or hydroxyl group); and n is 1 or 2.

(7) Japanese Patent Laid-Open Publication No. Hei 9-104674 describes a compound represented by the following formula:

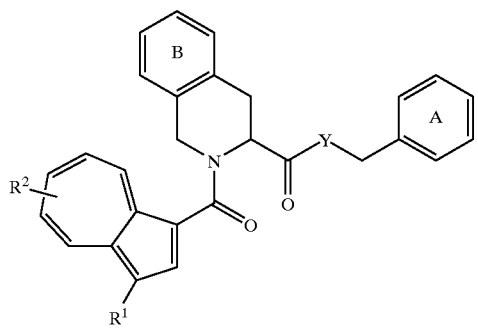

wherein X is a hydrogen or oxygen atom; Y is a nitrogen or oxygen atom which may or may not be alkylated or acylated; $R^1$ is a hydrogen atom, a lower alkyl group, a lower alkanoyl group, an alkyl group having a nitrogen atom, a carbamoyl group, a lower alkylthio group, a lower alkylsulfinyl group, a lower alkylsulfonyl group, or a (4-phenylpiperadine-1-yl) methyl group; $R^2$ is a hydrogen atom, a lower alkyl group, a lower alkyl group having a hydroxyl group, a lower alkanoyl group, or a lower alkoxy group; and the rings A and B are each a substituted or unsubstituted benzene ring.

(8) Japanese Patent Laid-Open Publication No. Hei 9-263585 describes a compound represented by the following formula:

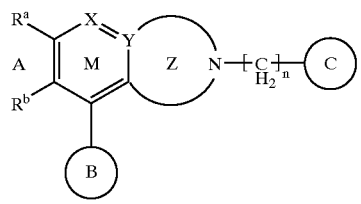

wherein the ring M is a heterocyclic ring in which the structural moiety —X=Y< is —N=C<, —CO—N<, or —CS—N<; Ra and Rb may together form the ring A, or Ra and Rb are each independently a hydrogen atom or a substituent of the ring M; the rings A and B are each independently a substituted or unsubstituted homocyclic or heterocyclic ring, provided that at least one of the rings A and B is a substituted or unsubstituted heterocyclic ring; the ring C is a substituted or unsubstituted homocyclic or heterocyclic ring; the ring Z is a substituted or unsubstituted ring; and n is an integer from 1 to 6.

(9) Japanese Patent Laid-Open Publication No. Hei 11-246559 describes a compound represented by the following formula:

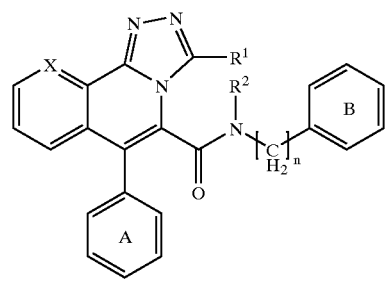

wherein X is a nitrogen atom or a CH group; $R^1$ is a hydrogen atom, a lower alkyl group, an aryl group, or an aralkyl group; $R^2$ is a hydrogen atom or a lower alkyl group; the rings A and B are each independently a substituted or unsubstituted benzene ring; and n is 1 or 2.

(10) Japanese Patent Laid-Open Publication No. 2000-139834 describes a compound represented by the following formula:

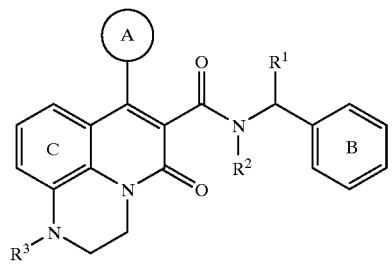

wherein $R^1$ and $R^2$ are each independently a hydrogen atom or an $C_1$ to $C_6$ alkyl group; $R^3$ is a hydrogen atom, a substituted or unsubstituted $C_1$ to $C_6$ alkylcarbonyl group, a substituted or unsubstituted $C_1$ to $C_6$ alkylsulfonyl group, a substituted or unsubstituted $C_1$ to $C_6$ alkyl group, a substituted or unsubstituted arylmethyl group or an alkoxycarbonyl group; the ring A is a homocyclic or heterocyclic ring which may include 1 through 3 independently selected substituents (any adjacent two of which may be bound to one another to form a ring); the ring B is a benzene ring which may include 1 through 5 substituents (any adjacent two of which may be bound to one another to form a ring); and the ring C is a benzene ring which may include 1 through 3 substituents (any adjacent two of which may be bound to one another to form a ring).

(11) Japanese Patent Laid-Open Publication No. 2000-247957 describes a compound represented by the following formula:

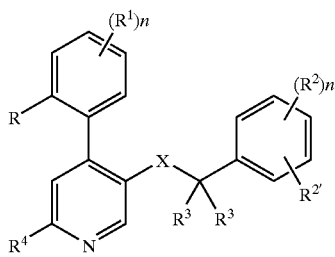

wherein R is a hydrogen atom or the like; $R^1$ is a hydrogen atom or the like; $R^2$ and $R^{2'}$ are each a hydrogen atom or the like; $R^3$ is a hydrogen atom or the like; $R^4$ is a hydrogen atom or the like; $R^5$ is a hydrogen atom or the like; $R^6$ is a hydrogen atom or the like; X is —C(O)N($R^5$)— or the like; n is an integer from 0 to 4; and m is 1 or 2.

(12) PCT pamphlet (International Patent Publication) No. WO00/50401 describes a compound represented by the following formula:

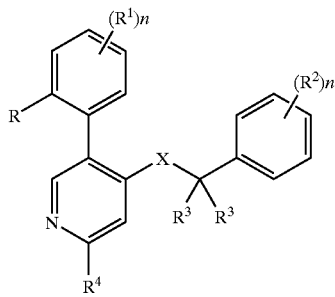

wherein R is a hydrogen atom or the like; $R^1$ is a hydrogen atom or the like; $R^2$ is a hydrogen atom or the like; $R^3$ is a hydrogen atom or the like; $R^4$ is a hydrogen atom or the like; $R^5$ is a hydrogen atom or the like; $R^6$ is a hydrogen atom or the like; X is —C(O)N($R^5$)— or the like; n is an integer from 0 to 4; and m is 1 or 2.

(13) PCT pamphlet (International Patent Publication) No. WO00/73279 describes a compound represented by the following formula:

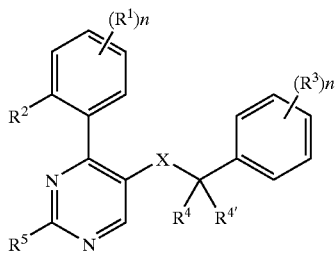

wherein $R^1$ is a hydrogen atom or the like; $R^2$ is a hydrogen atom or the like; $R^3$ is a hydrogen atom or the like; $R^4$ and $R^{4'}$ are each a hydrogen atom or the like; $R^5$ is a lower alkyl group or the like; n is an integer from 0 to 2; and X is —C(O)N($R^{4''}$)— or the like.

(14) PCT pamphlet (International Patent Publication) No. WO00/73278 describes a compound represented by the following formula:

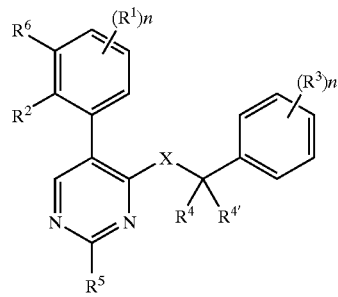

wherein $R^1$ is a hydrogen atom or the like; $R^2$ is a hydrogen atom or the like; $R^3$ is a hydrogen atom or the like; $R^4$ and $R^{4'}$ are each a hydrogen atom or the like; $R^5$ is a lower alkyl group or the like; $R^6$ is a hydrogen atom or the like; n is an integer from 0 to 2; and X is —C(O)N($R^{4''}$)— or the like.

DISCLOSURE OF THE INVENTION

At present, no effective tachykinin antagonists (in particular, NK1 receptor antagonists) are known that can serve as prophylactic or therapeutic agents against the above-described pathological conditions and at the same time meet requirements for pharmaceutical products, including safety, persistence of efficacy, pharmacokinetics, and pharmacological activities.

It is thus an objective of the present invention to provide a novel compound that acts as an effective tachykinin receptor antagonist and, in particular, as an NK1 receptor antagonist and can thus serve as a prophylactic or a therapeutic agent against various tachykinin receptor-related pathological conditions, including increased urinary frequency, incontinence of urine, vomiting, inflammation, allergies, respiratory tract disorders, pains, and central nervous system disorders.

The present inventors have discovered that fused bicyclic pyrimidine derivatives as represented by the following general formula (1), or salts thereof, can act as effective tachykinin receptor antagonists (in particular, as NK1 receptor antagonists):

(General Formula (1))

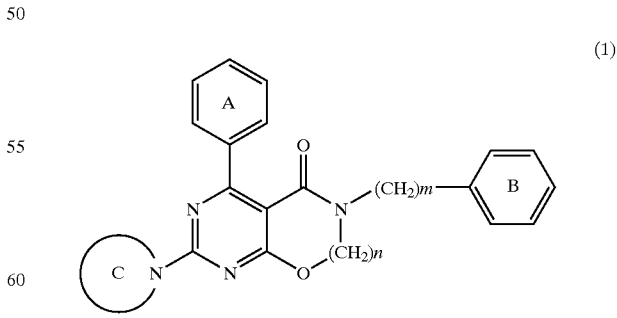

wherein the rings A and B are each a benzene ring that may include 1 through 3 substituents (any adjacent two of which may be bound to one anther to form a ring); the ring C is a nitrogen-containing ring; m is 1 or 2; and n is 2 or 3. As evidence, the present inventors have demonstrated in animal experiments that these compounds can effectively relieve dysuria, a tachykinin-mediated disorder. This discovery led the present inventors to ultimately complete the present invention.

Accordingly, the present invention provides the followings:

(I) A fused bicyclic pyrimidine derivative represented by the following general formula (1), or a salt thereof:

(General Formula (1))

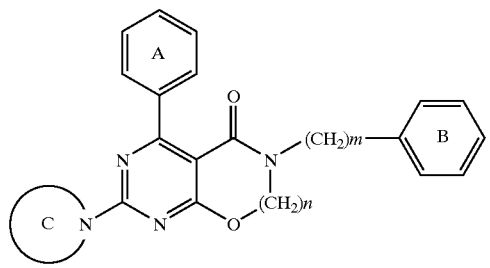

(1)

wherein the rings A and B are each a benzene ring, which may have 1 to 3 substituents (any adjacent two of which may be bound to one another to form a ring) that are each independently selected from the group consisting of a halogen atom, a $C_1$ to $C_6$ alkyl group, which may be substituted with a halogen atom, and a $C_1$ to $C_6$ alkoxyl group;

the ring C is a 5- to 7-membered nitrogen-containing ring, which may contain, aside from the nitrogen atom, 1 to 3 heteroatoms selected from the group consisting of a nitrogen atom, a sulfur atom, and an oxygen atom;

the ring C may further contain a substituent selected from the group consisting of a $C_1$ to $C_6$ alkyl group, a hydroxyl group, a $C_1$ to $C_6$ alkoxyl group, a formyl group, a $C_1$ to $C_6$ alkylcarbonyl group, a $C_1$ to $C_6$ alkoxycarbonyl group, a carbamoyl group, a mono- or di-substituted $C_1$ to $C_6$ alkylcarbamoyl group, a $C_1$ to $C_6$ alkylsulfonyl group, an amino group, a mono- or di-substituted $C_1$ to $C_6$ alkylamino group, a $C_1$ to $C_6$ alkylcarbonylamino group, a $C_1$ to $C_6$ alkoxycarbonylamino group, a $C_1$ to $C_6$ alkylsulfonylamino group, an oxo group, a 6-membered aromatic heterocyclic group, and a substituent represented by the following formula:

wherein the ring D is a 3- to 7-membered nonaromatic heterocyclic ring, which may contain, aside from the nitrogen atom, 1 to 3 heteroatoms selected from the group consisting of a nitrogen atom, a sulfur atom, and an oxygen atom and may further contain 1 or 2 oxo-substituted carbon atoms;

m is 1 or 2; and n is 2 or 3.

(II) The fused bicyclic pyrimidine derivative according to (I) above represented by the following general formula (1a), or a salt thereof:

(General Formula (1a))

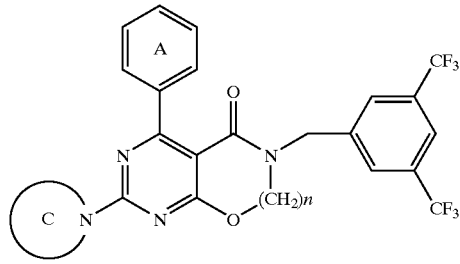

(1a)

wherein the ring A is a benzene ring, which may have 1 to 3 substituents (any adjacent two of which may be bound to one another to form a ring) that are each independently selected from the group consisting of a halogen atom, a $C_1$ to $C_6$ alkyl group, which may be substituted with a halogen atom, and a $C_1$ to $C_6$ alkoxyl group;

the ring C is a 5- to 7-membered nitrogen-containing ring, which may contain, aside from the nitrogen atom, 1 to 3 heteroatoms selected from the group consisting of a nitrogen atom, a sulfur atom, and an oxygen atom;

the ring C may further contain a substituent selected from the group consisting of a ($C_1$ to $C_6$ alkyl group, a hydroxyl group, a $C_1$ to $C_6$ alkoxyl group, a formyl group, a $C_1$ to $C_6$ alkylcarbonyl group, a $C_1$ to $C_6$ alkoxycarbonyl group, a carbamoyl group, a mono- or di-substituted $C_1$ to $C_6$ alkylcarbamoyl group, a $C_1$ to $C_6$ alkylsulfonyl group, an amino group, a mono- or di-substituted $C_1$ to $C_6$ alkylamino group, a $C_1$ to $C_6$ alkylcarbonylamino group, a $C_1$ to $C_6$ alkoxycarbonylamino group, a $C_1$ to $C_6$ alkylsulfonylamino group, an oxo group, a 6-membered aromatic heterocyclic group, and a substituent represented by the following formula:

wherein the ring D is a 3- to 7-membered nonaromatic heterocyclic ring, which may contain, aside from the nitrogen atom, 1 to 3 heteroatoms selected from the group consisting of a nitrogen atom, a sulfur atom, and an oxygen atom and may further contain 1 or 2 oxo-substituted carbon atoms; and n is 2 or 3.

(III) The fused bicyclic pyrimidine derivative according to (II) above, or a salt thereof, wherein in the general formula (1a), the ring C is represented by the following formula:

wherein $R^1$ is a hydroxyl group, a $C_1$ to $C_6$ alkoxy group, a formyl group, a $C_1$ to $C_6$ alkylcarbonyl group, a $C_1$ to $C_6$ alkoxycarbonyl group, a carbamoyl group, a mono- or di-substituted $C_1$ to $C_6$ alkylcarbamoyl group, a mono- or di-substituted $C_1$ to $C_6$ alkylamino group, a $C_1$ to $C_6$ alkylcarbonylamino group, a $C_1$ to $C_6$ alkoxycarbonylamino group, a $C_1$ to $C_6$ alkylsulfonylamino group, an oxo group, a 6-membered aromatic heterocyclic group, or a substituent represented by the following formula:

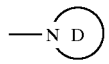

wherein the ring D is a 3- to 7-membered nonaromatic heterocyclic ring, which may contain, aside from the nitrogen atom, 1 to 3 heteroatoms selected from the group consisting of a nitrogen atom, a sulfur atom, and an oxygen atom and may further contain 1 or 2 oxo-substituted carbon atoms.

(IV) The fused bicyclic pyrimidine derivative according to (II) above, or a salt thereof, wherein in the general formula (1a), the ring C is represented by the following formula:

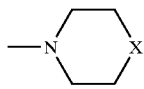

wherein X is —O— or —S(O)$_q$—; and q is 0, 1, or 2.

(V) The fused bicyclic pyrimidine derivative according to (II) above, or a salt thereof, wherein in the general formula (1a), the ring C is a group represented by the following formula:

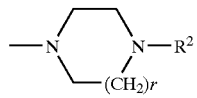

wherein $R^2$ is a hydrogen atom, a $C_1$ to $C_6$ alkyl group, a formyl group, a $C_1$ to $C_6$ alkylcarbonyl group, a $C_1$ to $C_6$ alkoxycarbonyl group, a carbamoyl group, a mono- or di-substituted $C_1$ to $C_6$ alkylcarbamoyl group or a $C_1$ to $C_6$ alkylsulfonyl group; and r is 1 or 2.

(VI) The fused bicyclic pyrimidine derivative according to (II) above, or a salt thereof, wherein in the general formula (1a), the ring C is represented by the following formula:

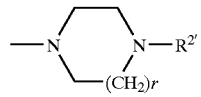

wherein $R^{2'}$ is an acetyl group or a methylsulfonyl group; and r is 1 or 2.

(VII) The fused bicyclic pyrimidine derivative according to (II) above, or a salt thereof, wherein in the general formula (1a) above, the ring C is represented by the following formula:

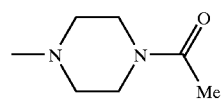

(VIII) The fused bicyclic pyrimidine derivative according to (VII) above, or a salt thereof, wherein in the general formula (1a) above, n is 3.

(IX) The compound according to (I) above, wherein the compound represented by the general formula (1) is 9-(4-acetylpiperazine-1-yl)-5-[3,5-bis(trifluoromethyl)benzyl]-7-(2-methylphenyl)-6-oxo-2,3,4,5-tetrahydro-6H-pyrimido[4,5-b][1,5]oxazocine.

(X) The compound according to (I) above, wherein the compound represented by the general formula (1) is 5-[3,5-bis(trifluoromethyl)benzyl]-9-(1,1-dioxothiomorpholine-4-yl)-7-(2-methylphenyl)-6-oxo-2,3,4,5-tetrahydro-6H-pyrimido[4,5-b][1,5]oxazocine.

(XI) The compound according to (I) above, wherein the compound represented by the general formula (1) is 9-(4-acetylhomopiperazine-1-yl)-5-[3,5-bis(trifluoromethyl)benzyl]-7-(2-methylphenyl)-6-oxo-2,3,4,5-tetrahydro-6H-pyrimido[4,5-b][1,5]oxazocine.

(XII) The compound according to (I) above, wherein the compound represented by the general formula (1) is 5-[3,5-bis(trifluoromethyl)benzyl]-7-(2-methylphenyl)-9-(4-methylpiperazine-1-yl)-6-oxo-2,3,4,5-tetrahydro-6H-pyrimido[4,5-b][1,5]oxazocine.

(XIII) A tachykinin receptor antagonist containing as an active ingredient the fused bicyclic pyrimidine derivative according to any one of (I) through (XII) above, or a salt thereof.

(XIV) An NK1 receptor antagonist containing as an active ingredient the fused bicyclic pyrimidine derivative according to any one of (I) through (XII) above, or a salt thereof.

(XV) A prophylactic or therapeutic agent for dysuria, including defective bladder functions such as increased urinary frequency and incontinence of urine, containing as an active ingredient the fused bicyclic pyrimidine derivative according to any of (I) through (XII) above, or a salt thereof.

(XVI) A prophylactic or therapeutic agent for disorders of digestive tract such as ulcerative colitis and Crohn's disease, containing as an active ingredient the fused bicyclic pyrimidine derivative according to any of (I) through (XII) above, or a salt thereof.

(XVII) A prophylactic or therapeutic agent for vomiting induced by exposure to X-ray, chemotherapy, pregnancy, migraine, postoperative pains, decreased gastrointestinal motility, and side effects of drugs, containing as an active ingredient the fused bicyclic pyrimidine derivative according to any of (I) through (XII) above, or a salt thereof.

(XVIII) A therapeutic agent for treating conditions, such as asthma, coughing, ache, migraine, tooth pain, and rheumatoid arthritis, containing as an active ingredient the fused bicyclic pyrimidine derivative according to any of (I) through (XII) above, or a salt thereof.

BEST MODE FOR CARRYING OUT THE INVENTION

The present invention will now be described in detail.

Rings A and B

In the general formula (1), the rings A and B each independently represent a benzene ring, which may include 1 to 3 substituents (any adjacent two of which substituents may be bound to one another to form a ring). The substituents on each of the rings A and B may be positioned at any possible position with the number of the substituents on each ring varying from about 1 to 3. Any adjacent two of these substituents may be bound to each other to form a ring. Examples of the substituents on the rings A and B include halogen atoms, $C_1$ to $C_6$ alkyl groups, which may be substituted with halogen atoms, and $C_1$ to $C_6$ alkoxyl groups.

Examples of the halogen atoms include fluorine atom, chlorine atom, bromine atom, and iodine atom.

Examples of the "$C_1$ to $C_6$ alkyl groups that may be substituted with halogen atoms" include methyl group, ethyl group, propyl group, isopropyl group, isobutyl group, sec-butyl group, tert-butyl group, fluoromethyl group, chloromethyl group, bromomethyl group, iodomethyl group, 1-fluoroethyl group, 1-chloroethyl group, 2-chloroethyl group, difluoromethyl group, trifluoromethyl group, trichloromethyl group, and 2,2,2-trifluoroethyl group.

Examples of the "$C_1$ to $C_6$ alkoxyl groups" include methoxy group, ethoxy group, propoxy group, isopropoxy group, isobutoxy group, sec-butoxy group, and tert-butoxy group.

Examples of the "rings in which two adjacent substituents are bound to each other to form a ring" include the followings:

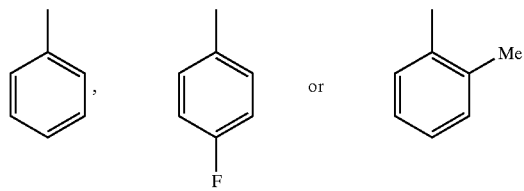

Ring A

Preferred examples of the ring A are those represented by the following formulae:

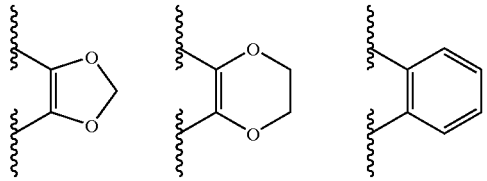

wherein $R^3$, $R^4$, and $R^5$ are each independently a fluorine atom, a chlorine atom, a methyl group, an ethyl group, a trifluoromethyl group, or a methoxy group.

Particularly preferred examples of the ring A are those represented by the following formulae:

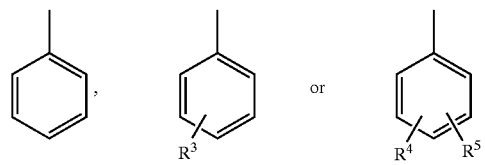

Ring B

Preferred examples of the ring B are those represented by the following formulae:

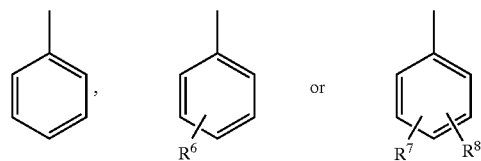

wherein $R^6$, $R^7$, and $R^8$ are each independently a fluorine atom, a chlorine atom, a methyl group, an ethyl group, a trifluoromethyl group, or a methoxy group.

Particularly preferred examples of the ring B are those represented by the following formulae:

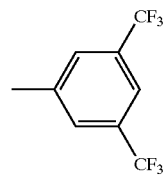

Ring C

The ring C is a 5- to 7-membered nitrogen-containing ring that may be substituted and may contain, aside from the nitrogen atom, 1 to 3 heteroatoms selected from the group consisting of a nitrogen atom, a sulfur atom, and an oxygen atom. Examples of "5- to 7-membered nitrogen-containing rings that may contain, aside from a nitrogen atom, 1 to 3 heteroatoms selected from the group consisting of a nitrogen atom, a sulfur atom, and an oxygen atom" include 5-membered aromatic heterocyclic rings that may contain, aside from a nitrogen atom, 1 to 3 heteroatoms selected from the group consisting of a nitrogen atom, a sulfur atom, and an oxygen atom (such as pyrrole, imidazole, pyrazole, triazole, and tetrazole rings) and 5- to 7-membered nonaromatic heterocyclic rings that may contain, aside from a nitrogen atom, 1 to 3 heteroatoms selected from the group consisting of a nitrogen atom, a sulfur atom, and an oxygen atom (such as tetrahydropyridine, dihydropyridine, tetrahydropyrazine, tetrahydropyrimidine, tetrahydropyridazine, dihydropyrrole, dihydroimidazole, dihydropyrazole, dihydrooxazole, dihydroisooxazole, piperidine, piperazine, hexahydropyrimidine, hexahydropyridazine, morpholine, thiomorpholine, homopiperidine, homopiperazine, pyrrolidine, imidazolidine, pyrazolidine, tetrahydrooxazole, tetrahydroisooxazole rings.).

Examples of "optional substituents on the ring C" include a $C_1$ to $C_6$ alkyl group, a hydroxyl group, a $C_1$ to $C_6$ alkoxy group, a formyl group, a $C_1$ to $C_6$ alkylcarbonyl group, a $C_1$ to $C_6$ alkoxycarbonyl group, a carbamoyl group, a mono- or di-substituted $C_1$ to $C_6$ alkylcarbamoyl group, a $C_1$ to $C_6$ alkylsulfonyl group, an amino group, a mono- or di-substituted $C_1$ to $C_6$ alkylamino group, a $C_1$ to $C_6$ alkylcarbonylamino group, a $C_1$ to $C_6$ alkoxycarbonylamino group, a $C_1$ to $C_6$ alkylsulfonylamino group, an oxo group, a 6-membered aromatic heterocyclic group, and a group represented by the following formula:

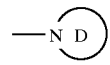

(wherein the ring D is a 3- to 7-membered nonaromatic heterocyclic ring that may contain, aside from the nitrogen atom, 1 to 3 heteroatoms selected from the group consisting of a nitrogen atom, a sulfur atom, and an oxygen atom and may further contain 1 or 2 oxo-substituted carbon atoms).

Examples of the "$C_1$ to $C_6$ alkyl group" include methyl group, ethyl group, propyl group, isopropyl group, isobutyl group, sec-butyl group, and tert-butyl group.

Examples of the "$C_1$ to $C_6$ alkoxy group" include methoxy group, ethoxy group, propoxy group, isopropoxy group, isobutoxy group, sec-butoxy group, and tert-butoxy group.

Examples of the "$C_1$ to $C_6$ alkylcarbonyl group" include acetyl group, propionyl group, and butyryl group.

Examples of the "$C_1$ to $C_6$ alkoxycarbonyl group" include methoxycarbonyl group, ethoxycarbonyl group, isopropoxycarbonyl group, and t-butoxycarbonyl group.

Examples of the "mono- or di-substituted $C_1$ to $C_6$ alkylcarbamoyl group" include methylcarbamoyl group, ethylcarbamoyl group, propylcarbamoyl group, isopropylcarbamoyl group, t-butylcarbamoyl group, hexylcarbamoyl group, dimethylcarbamoyl group, diethylcarbamoyl group, dipropylcarbamoyl group, diisopropylcarbamoyl group, dibutylcarbamoyl group, and dihexylcarbamoyl group.

Examples of the "$C_1$ to $C_6$ alkylsulfonyl group" include methylsulfonyl group, ethylsulfonyl group, and propylsulfonyl group.

Examples of the "mono- or di-substituted $C_1$ to $C_6$ alkylamino group" include methylamino group, ethylamino group, propylamino group, isopropylamino group, t-butylamino group, hexylamino group, dimethylamino group, diethylamino group, dipropylamino group, diisopropylamino group, dibutylamino group, and dihexylamino group.

Examples of the "$C_1$ to $C_6$ alkylcarbonylamino group" include acetylamino group, propionylamino group, and butyrylamino group.

Examples of the "$C_1$ to $C_6$ alkoxycarbonylamino group" include methoxycarbonylamino group, ethoxycarbonylamino group, t-butoxycarbonylamino group, and hexyloxycarbonylamino group.

Examples of the "$C_1$ to $C_6$ alkylsulfonylamino group" include methylsulfonylamino group, and ethylsulfonylamino group.

Examples of the "6-membered aromatic heterocyclic group" include pyridyl group, pyrazyl group, pyrimidyl group, and pyridazinyl group.

Examples of the "functional group represented by the following formula:

(wherein the ring D is a 3- to 7-membered nonaromatic heterocyclic ring that may contain, aside from the nitrogen atom, 1 to 3 heteroatoms selected from the group consisting of a nitrogen atom, a sulfur atom, and an oxygen atom and may further contain 1 or 2 oxo-substituted carbon atoms)" include azetidino group, pyrrolidino group, piperidino group, morpholino group, thiomorpholino group, piperazino group, 4-methylpiperazino group, homopiperazino group, 2-oxopyrrolidino group, 3-oxomorpholino group, and 2-oxomorpholino group.

Preferred examples of the ring C include those represented by the following formulae:

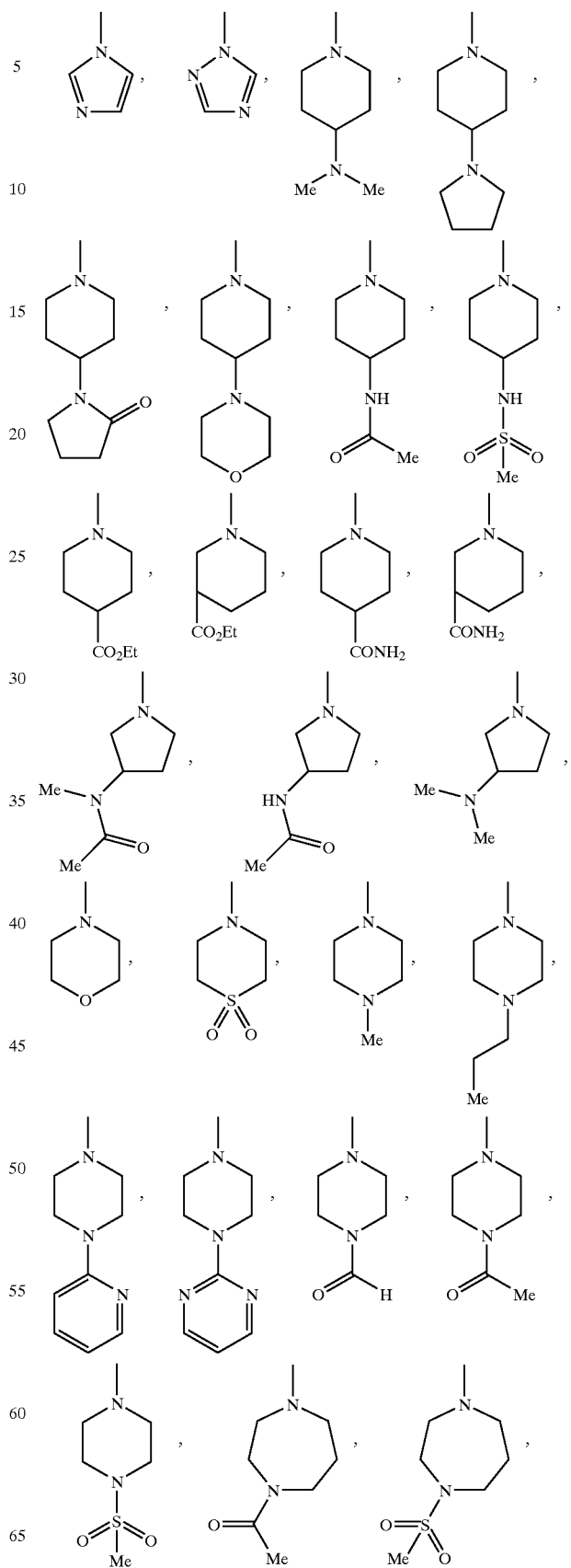

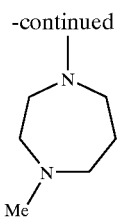

Of these, particularly preferred are those represented by the following formulae:

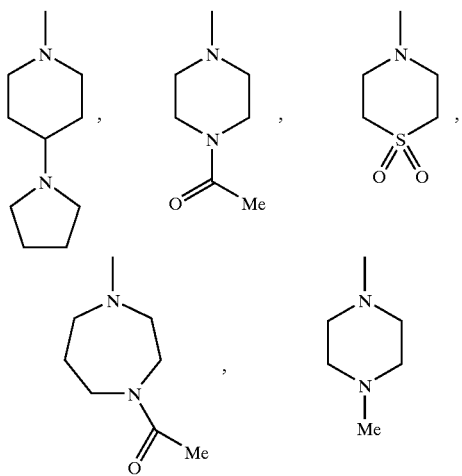

Of these, more preferred are those represented by the following formulae:

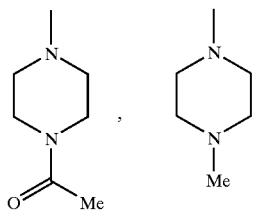

*m* m is 1 or 2, and preferably 1.

*n* n is 2 or 3, and preferably 3.

Preferred examples of the compounds of the present invention include 5-[3,5-bis(trifluoromethyl)benzyl]-9-(morpholine-4-yl)-6-oxo-7-phenyl-2,3,4,5-tetrahydro-6H-pyrimido[4,5-b][1,5]oxazocine; 5-[3,5-bis(trifluoromethyl)benzyl]-7-(2-fluorophenyl)-9-(morpholine-4-yl)-6-oxo-2,3,4,5-tetrahydro-6H-pyrimido[4,5-b][1,5]oxazocine; 5-[3,5-bis(trifluoromethyl)benzyl]-7-(2-methylphenyl)-9-(morpholine-4-yl)-6-oxo-2,3,4,5-tetrahydro-6H-pyrimido[4,5-b][1,5]oxazocine; 5-[3,5-bis(trifluoromethyl)benzyl]-7-(2-chlorophenyl)-9-(morpholine-4-yl)-6-oxo-2,3,4,5-tetrahydro-6H-pyrimido[4,5-b][1,5]oxazocine; 5-[3,5-bis(trifluoromethyl)benzyl]-7-(4-fluorophenyl)-9-(morpholine-4-yl)-6-oxo-2,3,4,5-tetrahydro-6H-pyrimido[4,5-b][1,5]oxazocine; 5-[3,5-bis(trifluoromethyl)benzyl]-7-(2,4-difluorophenyl)-9-(morpholine-4-yl)-6-oxo-2,3,4,5-tetrahydro-6H-pyrimido[4,5-b][1,5]oxazocine; 5-[3,5-bis(trifluoromethyl)benzyl]-7-(4-methoxyphenyl)-9-(morpholine-4-yl)-6-oxo-2,3,4,5-tetrahydro-6H-pyrimido[4,5-b][1,5]oxazocine; 5-[3,5-bis(trifluoromethyl)benzyl]-7-(2,4-dimethoxyphenyl)-9-(morpholine-4-yl)-6-oxo-2,3,4,5-tetrahydro-6H-pyrimido[4,5-b][1,5]oxazocine; 5-[3,5-bis(trifluoromethyl)benzyl]-7-[4-(dimethylamino)phenyl]-9-(morpholine-4-yl)-6-oxo-2,3,4,5-tetrahydro-6H-pyrimido[4,5-b][1,5]oxazocine; 5-[3,5-bis(trifluoromethyl)benzyl]-1-(2-methoxyphenyl)-9-(morpholine-4-yl)-6-oxo-2,3,4,5-tetrahydro-6H-pyrimido[4,5-b][1,5]oxazocine; 5-[3,5-bis(trifluoromethyl)benzyl]-6-oxo-7-phenyl-9-[4-(pyrrolidine-1-yl)piperidine-1-yl]-2,3,4,5-tetrahydro-6H-pyrimido[4,5-b][1,5]oxazocine; 5-[3,5-bis(trifluoromethyl)benzyl]-7-(2-methylphenyl)-6-oxo-9-[4-(pyrrolidine-1-yl)piperidine-1-yl]-2,3,4,5-tetrahydro-6H-pyrimido[4,5-b][1,5]oxazocine; 5-[3,5-bis(trifluoromethyl)benzyl]-7-(4-fluorophenyl)-6-oxo-9-[4-(pyrrolidine-1-yl)piperidine-1-yl]-2,3,4,5-tetrahydro-6H-pyrimido[4,5-b][1,5]oxazocine; 5-[3,5-bis(trifluoromethyl)benzyl]-7-(2-methylphenyl)-6-oxo-9-[4-(pyrimidine-2-yl)piperazine-1-yl]-2,3,4,5-tetrahydro-6H-pyrimido[4,5-b][1,5]oxazocine; 5-[3,5-bis(trifluoromethyl)benzyl]-7-(2-methylphenyl)-6-oxo-9-[4-(pyridine-2-yl)piperazine-1-yl]-2,3,4,5-tetrahydro-6H-pyrimido[4,5-b][1,5]oxazocine; 9-(4-acetylpiperazine-1-yl)-5-[3,5-bis(trifluoromethyl)benzyl]-7-(2-methylphenyl)-6-oxo-2,3,4,5-tetrahydro-6H-pyrimido[4,5-b][1,5]oxazocine; 5-[3,5-bis(trifluoromethyl)benzyl]-9-(4-formylpiperazine-1-yl)-7-(2-methylphenyl)-6-oxo-2,3,4,5-tetrahydro-6H-pyrimido[4,5-b][1,5]oxazocine; 5-[3,5-bis(trifluoromethyl)benzyl]-9-(imidazole-1-yl)-7-(2-methylphenyl)-6-oxo-2,3,4,5-tetrahydro-6H-pyrimido[4,5-b][1,5]oxazocine; 5-[3,5-bis(trifluoromethyl)benzyl]-7-(2-methylphenyl)-6-oxo-9-(1,2,4-tetrazole-1-yl)-2,3,4,5-tetrahydro-6H-pyrimido[4,5-b][1,5]oxazocine; 5-[3,5-bis(trifluoromethyl)benzyl]-9-(1,1-dioxothiomorpholine-4-yl)-7-(2-methylphenyl)-6-oxo-2,3,4,5-tetrahydro-6H-pyrimido[4,5-b][1,5]oxazocine; 5-[3,5-bis(trifluoromethyl)benzyl]-9-[3-(ethoxycarbonyl)piperidine-1-yl]-7-(2-methylphenyl)-6-oxo-2,3,4,5-tetrahydro-6H-pyrimido[4,5-b][1,5]oxazocine; 5-[3,5-bis(trifluoromethyl)benzyl]-9-[4-(ethoxycarbonyl)piperidine-1-yl]-7-(2-methylphenyl)-6-oxo-2,3,4,5-tetrahydro-6H-pyrimido[4,5-b][1,5]oxazocine; 5-[3,5-bis(trifluoromethyl)benzyl]-9-(3-carbamoylpiperidine-1-yl)-7-(2-methylphenyl)-6-oxo-2,3,4,5-tetrahydro-6H-pyrimido[4,5-b][1,5]oxazocine; 5-[3,5-bis(trifluoromethyl)benzyl]-9-(4-carbamoylpiperidine-1-yl)-7-(2-methylphenyl)-6-oxo-2,3,4,5-tetrahydro-6H-pyrimido[4,5-b][1,5]oxazocine; 5-[3,5-bis(trifluoromethyl)benzyl]-9-[3-(dimethylamino)pyrrolidine-1-yl]-7-(2-methylphenyl)-6-oxo-2,3,4,5-tetrahydro-6H-pyrimido[4,5-b][1,5]oxazocine; 5-[3,5-bis(trifluoromethyl)benzyl]-9-(4-methylhomopiperazine-1-yl)-7-(2-methylphenyl)-6-oxo-2,3,4,5-tetrahydro-6H-pyrimido[4,5-b][1,5]oxazocine; 5-[3,5-bis(trifluoromethyl)benzyl]-9-[3-(acetylamino)pyrrolidine-1-yl]-7-(2-methylphenyl)-6-oxo-2,3,4,5-tetrahydro-6H-pyrimido[4,5-b][1,5]oxazocine; 9-(4-acetylpiperazine-1-yl)-5-[3,5-bis(trifluoromethyl)benzyl]-7-(4-fluorophenyl)-6-oxo-2,3,4,5-tetrahydro-6H-pyrimido[4,5-b][1,5]oxazocine; 9-(4-acetylpiperazine-1-yl)-5-[3,5-bis(trifluoromethyl)benzyl]-7-(2-methoxyphenyl)-6-oxo-2,3,4,5-tetrahydro-6H-pyrimido[4,5-b][1,5]oxazocine; 9-(4-acetylpiperazine-1-yl)-5-[3,5-bis(trifluoromethyl)benzyl]-6-oxo-7-phenyl-2,3,4,5-tetrahydro-6H-pyrimido[4,5-b][1,5]oxazocine; 9-(4-acetylpiperazine-1-yl)-5-[3,5-bis(trifluoromethyl)benzyl]-7-(4-fluoro-2-methylphenyl)-6-oxo-2,3,4,5-tetrahydro-6H-pyrimido[4,5-b][1,5]oxazocine;

8-(4-acetylpiperazine-1-yl)-4-[3,5-bis(trifluoromethyl)benzyl]-6-(2-methylphenyl)-5-oxo-2,3,4,5-tetrahydropyrimido[5,4-f][1,4]oxazepine; 5-[3,5-bis(trifluoromethyl)benzyl]-7-(2-methylphenyl)-6-oxo-9-[4-(2-oxopyrrolidine-1-yl)piperidine-1-yl]-2,3,4,5-tetrahydro-6H-pyrimido[4,5-b][1,5]oxazocine; 5-[3,5-bis(trifluoromethyl)benzyl]-7-(2-methylphenyl)-9-[4-(morpholine-4-yl)piperidine-1-yl]-6-oxo-2,3,4,5-tetrahydro-6H-pyrimido[4,5-b][1,5]oxazocine; 5-[3,5-bis(trifluoromethyl)benzyl]-9-[4-(dimethylamino)piperidine-1-yl]-7-(2-methylphenyl)-6-oxo-2,3,4,5-tetrahydro-6H-pyrimido[4,5-b][1,5]oxazocine; 5-[3,5-bis(trifluoromethyl)benzyl]-7-(2-methylphenyl)-6-oxo-9-[4-(piperidine-1-yl)piperidine-1-yl]-2,3,4,5-tetrahydro-6H-pyrimido[4,5-b][1,5]oxazocine; 9-[4-(acetylamino)piperidine-1-yl]-5-[3,5-bis(trifluoromethyl)benzyl]-7-(2-methylphenyl)-6-oxo-2,3,4,5-tetrahydro-6H-pyrimido[4,5-b][1,5]oxazocine; 5-[3,5-bis(trifluoromethyl)benzyl]-9-[4-(methylsulfonylamino)piperidine-1-yl]-7-(2-methylphenyl)-6-oxo-2,3,4,5-tetrahydro-6H-pyrimido[4,5-b][1,5]oxazocine; 5-[3,5-bis(trifluoromethyl)benzyl]-9-[4-(methylsulfonyl)piperazine-1-yl]-7-(2-methylphenyl)-6-oxo-2,3,4,5-tetrahydro-6H-pyrimido[4,5-b][1,5]oxazocine; 5-[3,5-bis(trifluoromethyl)benzyl]-9-[4-(methylsulfonyl)homopiperazine-1-yl]-7-(2-methylphenyl)-6-oxo-2,3,4,5-tetrahydro-6H-pyrimido[4,5-b][1,5]oxazocine; 9-(4-acetylhomopiperazine-1-yl)-5-[3,5-bis(trifluoromethyl)benzyl]-7-(2-methylphenyl)-6-oxo-2,3,4,5-tetrahydro-6H-pyrimido[4,5-b][1,5]oxazocine; 9-[3-(acetylamino)-3-methylpyrrolidine-1-yl]-5-[3,5-bis(trifluoromethyl)benzyl]-7-(2-methylphenyl)-6-oxo-2,3,4,5-tetrahydro-6H-pyrimido[4,5-b][1,5]oxazocine; 5-[3,5-bis(trifluoromethyl)benzyl]-9-(1,1-dioxothiomorpholine-4-yl)-7-(2-methoxyphenyl)-6-oxo-2,3,4,5-tetrahydro-6H-pyrimido[4,5-b][1,5]oxazocine; and 5-[3,5-bis(trifluoromethyl)benzyl]-7-(2-methylphenyl)-9-(4-methylpiperazine-1-yl)-6-oxo-2,3,4,5-tetrahydro-6H-pyrimido[4,5-b][1,5]oxazocine.

Salts

Examples of pharmaceutically acceptable salts of the compounds of the present invention include those formed with inorganic acids, such as hydrochloric acid, hydrobromic acid, sulfuric acid, and nitric acid, and those formed with organic acids, such as acetic acid, maleic acid, fumaric acid, succinic acid, lactic acid, malic acid, tartaric acid, citric acid, methanesulfonic acid, p-toluenesulfonic acid, salicylic acid, stearic acid, and palmitic acid.

The compounds of the present invention or salts thereof may also exist in the form of hydrates or solvates. The present invention encompasses any hydrates or solvates formed by the fused bicyclic pyrimidine derivatives of the general formula (1), including the preferred compounds specifically mentioned above, or salts thereof. Examples of the solvents that can form solvates include methanol, ethanol, isopropanol, acetone, ethyl acetate, methylene chloride, and diisopropylether.

Aside from racemic mixtures, the compounds of the present invention or salts thereof may be provided in the form of optically active forms, stereoisomers, or atrop isomers.

Various synthetic techniques may be used to produce the compounds of the present invention. One commonly used production process of the compounds of the present invention or salts thereof is described below.

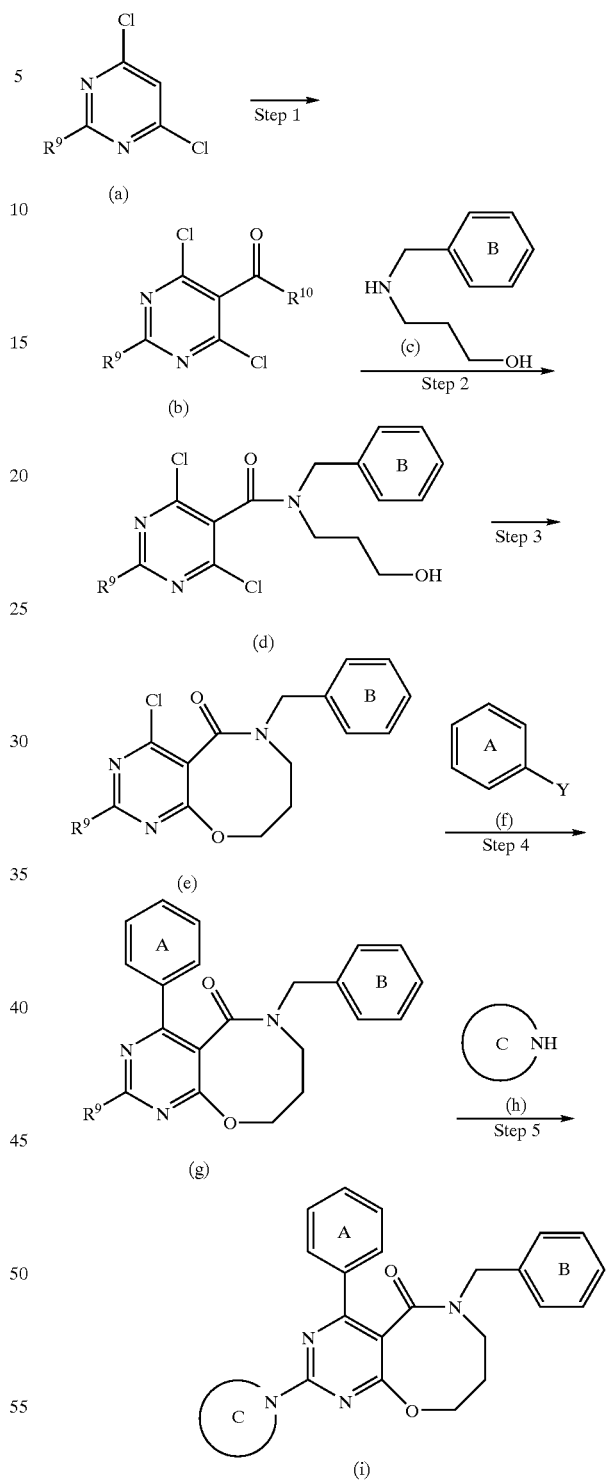

(Step 1)

In this step, a carbonyl group is introduced into a compound (a) (wherein $R^9$ is a leaving group that is eliminated later in Step 5 of the process, such as a halogen atom, a $C_1$ to $C_6$ alkylthio group, an arylthio group, a $C_1$ to $C_6$ alkylsulfonyl group, or an arylsulfonyl group, or $R^9$ is the ring C (the ring C is as described above)) to generate a compound (b) (wherein $R^9$ is as described above; $R^{10}$ is a hydroxyl group, a halogen atom, 1-imidazolyl group, 4-nitrophenoxy group, imidoyloxy succinate group, a $C_1$ to $C_6$ alkoxyl group, or a benzyloxy group). In this process, the compound (b) is generated by first treating the compound (a) with a base and then reacting the product with a compound that serve as a source of carbonyl group. The base for use in this process may be a bulky base, such as lithium diisopropylamide. The process is generally carried out at a temperature of −100° C. to 20° C., and preferably at a temperature of −100° C. to −50° C. The compound that serves as the source of carbonyl group for use in this process may be a halide of a carboxylic acid, an imidazolide of a carboxylic acid, an active ester of a carboxylic acid, an acid hydride, an orthoester or carbon dioxide. When $R^{10}$ is a hydroxyl group, the compound (a) is first treated with the above-described base and carbon dioxide is used as the source of carbonyl group. The process is terminated using a proper acid (e.g., hydrochloric acid).

(Step 2)

In this step, the compound (b) (wherein $R^9$ and $R^{10}$ are as described above) and the compound (c) (wherein the ring B is as described above) are allowed to undergo condensation to generate a compound (d) (wherein $R^9$ and the ring B are as described above). When $R^{10}$ is a hydroxyl group, a suitable condensation agent for use in the condensation reaction in this step may be dicyclohexylcarbodiimide (DCC), 3-ethyl-1-(3-dimethylaminopropyl)carbodimide hydrochloride (EDCI), or dimethylimidazolinium chloride (DMC). These condensation agents may be added in the form of a solid product or a solution in a proper solvent. A base may be used in the condensation reaction, including alkali carbonates, such as sodium hydrogen carbonate, or potassium carbonate, and tertially amines, such as triethylamine, diisopropylethylamine, N-methylmorpholine, diazabicyclo[5.4.0]-7-undecene, pyridine, 4-dimethylaminopyridine, or 1,8-bis(dimethylamino)naphthalene. The solvent for use in the condensation reaction may be any inert solvent that does not take part in the reaction, including N,N-dimethylformamide, N,N-dimethylacetamide, dimethylsulfoxide, acetonitrile, tetrahydrofuran, dioxane, ethyl ether, dimethoxyethane, ethylacetate, and dichloromethane. The condensation reaction may be carried out at −20° C. to 80° C. When the compound (b) for use in the condensation reaction in this step is any of a halide of a carboxylic acid, an imidazolide of a carboxylic acid, or an active ester of a carboxylic acid, in which $R^{10}$ is a halogen atom, a 1-imidazolyl group, a 4-nitrophenoxy group or an imidoyloxy succinate group, the reaction can be carried out by allowing the reactants to react in the presence or absence of an organic base, such as triethylamine, diisopropylethylamine, pyridine or 4-dimethylaminopyridine, or an inorganic base, such as sodium hydrogen carbonate or potassium carbonate, in a solvent, such as N,N-dimethylformamide, N,N-dimethylacetamide, dimethylsulfoxide, acetonitrile, tetrahydrofuran, dioxane, ethyl ether, dimethoxyethane, ethylacetate, toluene or dichloromethane, at −20° C. to 80° C. for 30 min. to 48 hours. When $R^{10}$ is a $C_1$ to $C_6$ ester residue such as an alkoxyl group and a benzyloxy group in the condensation reaction in this step, the reaction can be carried out by allowing the reactants to react in the presence or absence of trimethylaluminum or tetraisopropoxytitanium or in the presence or absence of an acidic or a basic catalyst, such as p-toluenesulfonic acid, sodium methoxide, potassium t-butoxide, or sodium hydride, in a solvent, such as N,N-dimethylformamide, N,N-dimethylacetamide, dimethylsulfoxide, acetonitrile, tetrahydrofuran, dioxane, toluene, xylene, mesitylene, pyridine, quinoline, or dichloromethane, at 15° C. to 150° C. for 30 min. to 48 hours.

(Step 3)

In this step, the compound (d) (wherein $R^9$ and the ring B are as described above) is cyclized to generate a compound (e) (wherein $R^9$ and the ring B are as described above). The step may be carried out by allowing the cyclization to take place in the presence or absence of an organic base, such as sodium-tert-butoxide or potassium-tert-butoxide, or an inorganic base, such as sodium hydride, potassium carbonate, sodium carbonate, cesium carbonate or sodium acetate, in a solvent, such as N,N-dimethylformamide, N,N-dimethylacetamide, dimethylsulfoxide, acetonitrile, tetrahydrofuran, dioxane, toluene, xylene, mesitylene, pyridine, quinoline, or dichloromethane, at 0° C. to 150° C. for 30 min. to 48 hours.

(Step 4)

In this step, the compound (e) (wherein $R^9$ and the ring B are as described above) and a compound (f) (wherein the ring A is as described above, Y is a halogen atom, $OSO_2R^{11}$ (wherein $R^{11}$ is a $C_1$ to $C_6$ alkyl group, which may be substituted with halogen atoms), $B(R^{12})_2$ (wherein the two $R^{12}$ substituents are each independently a hydroxyl group, a $C_1$ to $C_6$ alkyl group or a $C_1$ to $C_6$ alkoxyl group, or $R^{12}$ substituents may be bound to each other to form a ring), Li, MgBr, or ZnCl) are allowed to undergo either a cross-coupling reaction in the presence of a transitional metal catalyst, such as a palladium or nickel complex, or a Grignard reaction to generate a compound (g) (wherein $R^9$ and the rings A and B are as described above). Preferably, the process is carried out by using an inert solvent that does not take part in the process. Examples of the solvent include N,N-dimethylformamide, N,N-dimethylacetamide, dimethylsulfoxide, acetonitrile, tetrahydrofuran, dioxane, dichloromethane, toluene, ethanol or water. These solvents may be used individually or may be mixed with one another in any proportion. Examples of the palladium complexes for use in the process include palladium chloride, palladium acetate, acetylacetonato palladium, and tetrakis(triphenylphosphine)palladium. Examples of the nickel complexes for use in the process include bis(acetylacetonato)nickel, bis(1,5-cyclooctadiene)nickel, and tetrakis(triphenylphosphine)nickel. Each of these palladium or nickel complexes is used in an amount of 0.001 to 1 equivalent, preferably in an amount of 0.01 to 0.1 equivalents, with respect to the compound (e). When it is desired to use a ligand for the palladium or nickel complex in the process, the ligand may be triphenylphosphine, tri-o-tolylphosphine, tri-2-furylphosphine, 1,2-bis(diphenylphosphino)ethane, 1,1'-bis(diphenylphosphino)ferrocene, or 2,2'-bis(diphenylphosphino)-1,1'-binaphthyl. Each of these ligands is used in an amount of 0.2 to 5 equivalents, preferably in an amount of 0.3 to 3 equivalents, with respect to the palladium or nickel complex. Preferably, the process is carried out in the presence of a proper base. Among such bases are organic bases, including triethylamine, tributylamine, diisopropylethylamine, N-methylmorpholine, pyridine, lutidine, and collidine, and inorganic bases, including sodium hydrogen carbonate, sodium carbonate, potassium carbonate, calcium carbonate, cesium carbonate, and tripotassium phosphate. Each of these bases is used in an amount of 1 to 20 equivalents, preferably in an amount of 2 to 10 equivalents, with respect to the compound (e). The cross-coupling reaction in this step is carried out by allowing the reactants to undergo the reaction at 15 to 150° C., preferably at 50 to 120° C., for 30 min. to 24 hours.

(Step 5)

In this step, the compound (g) (wherein $R^9$ and the rings A and B are as described above) is reacted with a compound (h) to generate a compound (i) (wherein $R^9$ and the rings A and B are as described above). (This step is omitted when $R^9$ is the ring C.) The process can be carried out by using the compound (h) in an amount of 1 to 20 equivalents with respect to the compound (g) and allowing the reaction to proceed in the presence or absence of a base at 80 to 200° C., preferably at 100 to 150° C., for 30 min. to 24 hours. A base may preferably be used, including organic bases, such as trimethylamine, tributylamine, diisopropylethylamine, N-methylmorpholine, pyridine, lutidine, collidine, and N,N-dimethylaniline, and inorganic bases, such as sodium hydrogen carbonate, sodium carbonate, potassium carbonate, calcium carbonate, cesium carbonate, and tripotassium phosphate. When it is desired to use a solvent, such a solvent may be any inert solvent that does not take part in the reaction, including N,N-dimethylformamide, N,N-dimethylacetamide, sulfolane, acetonitrile, tetrahydrofuran, dioxane, xylene, toluene, ethanol, or water.

The compounds (1) of the present invention can be isolated/purified by ordinary means (for example, extraction, recrystallization, distillation, and chromatography). When the resulting compounds tend to form salts, such salts can be produced by ordinary techniques or equivalent techniques (for example, neutralization).

The compounds (1) of the present invention or salts thereof act as tachykinin receptor antagonists and, in particular, as NK1 receptor antagonists and are thus useful as:

prophylactic or therapeutic agents for dysuria, including defective bladder functions such as increased urinary frequency and incontinence of urine;

prophylactic or therapeutic agents for disorders of digestive tract such as ulcerative colitis and Crohn's disease;

prophylactic or therapeutic agents for vomiting induced by exposure to X-ray, chemotherapy, pregnancy, migraine, postoperative pains, decreased gastrointestinal motility, and side effects of drugs;

prophylactic or therapeutic agents for vomiting induced by exposure to X-ray, chemotherapy, pregnancy, migraine, postoperative pains, decreased gastrointestinal motility, and side effects of drugs; and therapeutic agents for asthma, coughing, ache, migraine, tooth pain, rheumatoid arthritis and other conditions.

The compounds (1) of the present invention or salts thereof may be used individually, or they may be formed into pharmaceutical compositions along with one or more pharmaceutically acceptable adjuvants. Specifically, the compounds of the present invention may be mixed with pharmaceutically acceptable carriers, excipients (such as starch, lactose, calcium phosphate, and calcium carbonate), lubricants (such as magnesium stearate, calcium stearate, talc, and stearic acid), binders (such as starch, cellulose crystals, carboxymethylcellulose, gum Arabic, polyvinylpyrrolidone, and alginic acid), disintegrating agents (such as talc, carboxymethylcellulose, and calcium), and diluents (such as physiological saline, and aqueous solutions of glucose, mannitol and lactose). Using ordinary techniques, the compounds of the present invention may be prepared as tablets, capsules, granules, powders, fine granules, ampules, or injections for oral or parenteral administration. While the dosage of the compounds (1) of the present invention or salts thereof may vary depending on the type of salt, route of administration, and age and conditions of patients, a typical dose for humans and other mammals, for example, is in the range of 0.0001 to 300 mg/kg/day as measured by the amount of the compounds (1) of the present invention or salts thereof. The compounds (1) or salts thereof may be administered in a single dose or several doses each day.

EXAMPLES

The present invention will now be described in detail with reference to Examples, Reference Examples, and Test Examples, as will an exemplary production process of a starting material of the compounds (1) of the present invention, which is also a novel compound. It should be appreciated that the compounds of the present invention are not limited to those described in the following examples and may be modified without departing from the scope and the spirit of the invention.

Reference Example 1

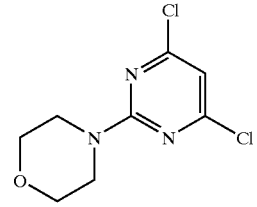

2-bromoethylether (3.65 g), potassium carbonate (8.29 g), and N,N-dimethylformamide (75 mL) were added to 2-amino-4,6-dichloropyrimidine (2.46 g), and the mixture was refluxed for 3 hours while heated. Subsequently, the reaction mixture was diluted with ethyl acetate, was washed with water, and was dried over anhydrous sodium sulfate. The solvent was removed and the resulting residue was purified on a silica gel column chromatography (hexane:ethyl acetate=5:1) to obtain 4,6-dichloro-2-(morpholine-4-yl)pyrimidine (985 mg, 28%).

MS(EI)m/z: 233(M$^+$) HRMS(EI): Calcd for $C_8H_9Cl_2N_3O$: 233.0123; found: 233.0152.

Reference Example 2

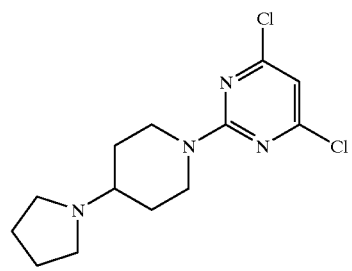

4 mol/L hydrogen chloride-dioxane (3.3 mL) was added to 4-(pyrrolidine-1-yl)piperidine (2.01 g) and the mixture was stirred at room temperature for 1 hour. Cyanamid (1.10 g) and n-butanol (20 mL) were then added and the mixture was stirred at 120° C. for 3 hours. The solvent was removed to obtain 4-(pyrrolidine-1-yl)piperidine-1-carboxyamidine hydrochloride (3.00 g, 99%). Subsequently, sodium metal (550 mg) is dissolved in ethanol (30 mL), and the resulting 4-(pyrrolidine-1-yl)piperidine-1-carboxyamidine hydrochloride (2.80 g) was added along with diethyl malonate (1.93 g) thereto. The mixture was stirred for 5 hours while heated. The mixture was then allowed to cool and 3 mol/L hydrogen chloride-ethyl acetate (5 mL) was added to adjust pH to 1. The solvent was removed to obtain a residue. Phosphorus oxychloride (70 mL) was then added to this residue and the mixture was refluxed for 2 hours while heated. Following removal of the solvent, water and then sodium hydrogen carbonate was added to the residue to adjust pH to 10. The mixture was extracted with ethyl acetate and the extract was dried over anhydrous sodium sulfate. The solvent was removed and the resulting residue was purified on a silica gel column chromatography (ethyl acetate:methanol=3:1) to obtain 4,6-dichloro-2-[4-(pyrrolidine-1-yl)piperidine-1-yl]pyrimidine (787 mg, 22%).

MS(EI)m/z: 300(M$^+$) HRMS(EI): Calcd for $C_{13}H_{18}Cl_2N_4$: 300.0909; found: 300.0923.

Reference Example 3

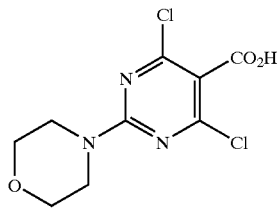

To a tetrahydrofuran solution of lithium diisopropylamide (which was prepared by diluting diisopropylamine (0.7 mL) with tetrahydrofuran (10 mL), followed by the addition of n-butyllithium (3.1 mL, 1.6 mol/L hexane solution) at −20° C. and then stirring at −20° C. for 1 hour), a tetrahydrofuran solution of 4,6-dichloro-2-(morpholine-4-yl)pyrimidine (953 mg) (5 mL) was added at −78° C. and the mixture was stirred for 4 hours. Carbon dioxide was then bubbled through the reaction mixture for 10 min. and water was added. The temperature of the mixture was then allowed to rise to room temperature. Following the addition of 2 mol/L hydrochloric acid (8 mL) to adjust pH to 1, the mixture was extracted with ethyl acetate and the extract was dried over anhydrous sodium sulfate. The solvent was removed and the residue was washed with diisopropylether to obtain 4,6-dichloro-2-(morpholine-4-yl)pyrimidine-5-carboxylic acid (1.15 g, 100%).

MS(EI)m/z: 277(M$^+$) HRMS(EI): Calcd for $C_9H_9Cl_2N_3O_3$: 277.0021; found: 277.0038.

Reference Example 4

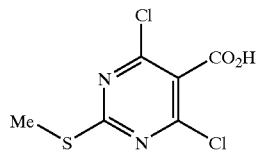

In a similar manner to Reference Example 3, 4,6-dichloro-2-(methylthio)pyrimidine (2.70 g) was used to obtain 4,6-dichloro-2-(methylthio)pyrimidine-5-carboxylic acid (1.93 g, 58%).

MS(EI)m/z: 238(M$^+$) HRMS(EI): Calcd for $C_6H_4Cl_2N_2O_2S$: 237.9371; found: 237.9383.

Reference Example 5

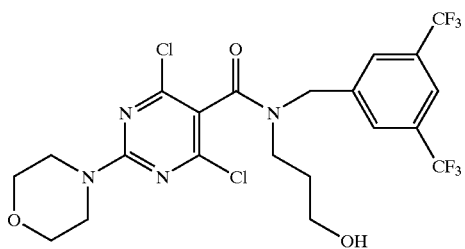

4,6-dichloro-2-(morpholine-4-yl)pyrimidine-5-carboxylic acid (Compound of Reference Example 3; 1.10 g) and N,N-dimethylformamide (3 droplets) were added to thionyl chloride (3.0 mL). While the mixture was refluxed for 2 hour. The reaction mixture was then distilled under reduced pressure to obtain a yellow residue.

3-(3,5-bis(trifluoromethyl)benzylamino)propanol (prepared according to the method described in Japanese Patent Laid-Open Publication No. Hei 9-263585; 1.25 g) and triethylamine (1.7 mL) were dissolved in tetrahydrofuran (40 mL). While the solution was chilled on an ice bath, a tetrahydrofuran solution of the yellow residue (4 mL) was added. After stirred for 1 hour, the mixture was further stirred for additional 3 hours at room temperature. The reaction mixture was diluted with ethyl acetate, was sequentially washed with water and a saturated aqueous solution of sodium chloride, and was then dried over anhydrous sodium sulfate. Following removal of the solvent, the residue was purified on a silica gel column chromatography (ethyl acetate:hexane=1:1) to obtain N-[3,5-bis(trifluoromethyl)benzyl]-4,6-dichloro-2-(morpholine-4-yl)pyrimidine-5-carboxylic acid amide (1.83 g, 82%).

MS(FAB$^+$) m/z: 561 (M+H$^+$) HRMS(FAB$^+$): Calcd for $C_{21}H_{21}Cl_2F_6N_4O_3$: 561.0895; found: 561.0897.

Reference Example 6

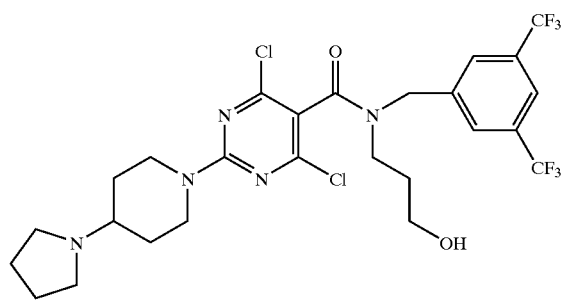

Following similar procedures to those described in Reference Example 3 and then those in Reference Example 5, 4,6-dichloro-2-[4-(pyrrolidine-1-yl)piperidine-1-yl]pyrimidine (Compound of Reference Example 2; 787 mg) was used to obtain N-[3,5-bis(trifluoromethyl)benzyl]-4,6-dichloro-2-[4-(pyrrolidine-1-yl)piperidine-1-yl]pyrimidine-5-carboxylic acid amide (1.30 g, 79%).

MS(FAB+) m/z: 628 (M+H+) HRMS(FAB+): Calcd for $C_{26}H_{30}Cl_2F_6N_5O_2$: 628.1681; found: 628.1658.

Reference Example 7

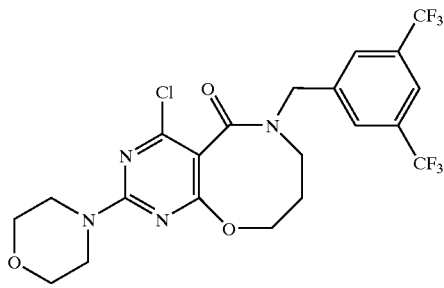

N-[3,5-bis(trifluoromethyl)benzyl]-4,6-dichloro-2-(morpholine-4-yl)pyrimidine-5-carboxylic acid amide (Compound of Reference Example 5; 1.77 g) was dissolved in tetrahydrofuran (30 mL). To this solution, sodium hydride (150 mg, 60% oil suspension) was added and the resulting mixture was refluxed for 3 hours while heated. Subsequently, the mixture was allowed to cool and water was added. The mixture was then diluted with ethyl acetate, was washed with a saturated aqueous solution of sodium chloride, and was then dried over anhydrous sodium sulfate. The solvent was removed and the resulting residue was purified on a silica gel column chromatography (ethyl acetate:hexane=2:1) to obtain 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (1.17 g, 71%).

MS(EI)m/z: 524(M+) HRMS(EI): Calcd for $C_{21}H_{19}ClF_6N_4O_3$: 524.1050; found: 524.1030.

Reference Example 8

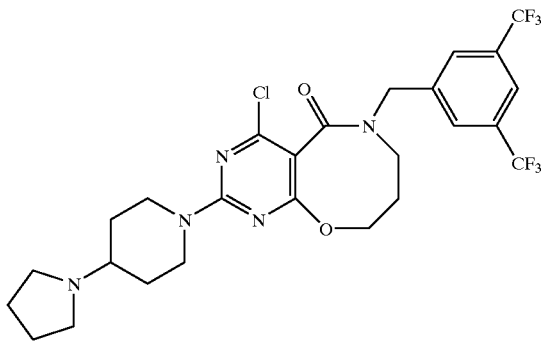

In a similar manner to Reference Example 7, N-[3,5-bis(trifluoromethyl)benzyl]-4,6-dichloro-2-[4-(pyrrolidine-1-yl)piperidine-1-yl]pyrimidine-5-carboxylic acid amide (Compound of Reference Example 6; 1.23 g) was used to obtain 5-[3,5-bis(trifluoromethyl)benzyl]-7-chloro-6-oxo-9-[4-(pyrrolidine-1-yl)piperidine-1-yl]-2,3,4,5-tetrahydro-6H-pyrimido[4,5-b][1,5]oxazocine (180 mg, 16%).

MS(EI)m/z: 591(M+) HRMS(EI): Calcd for $C_{26}H_{28}ClF_6N_5O_2$: 591.1836; found: 591.1826.

Reference Example 9

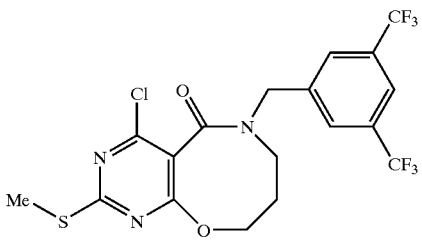

4,6-dichloro-2-(methylthio)pyrimidine-5-carboxylic acid (Compound of Reference Example 4; 14.0 g) and N,N-dimethylformamide (3 droplets) were added to thionyl chloride (40 mL). While heated, the mixture was refluxed for 2 hour. The reaction mixture was then distilled under reduced pressure to obtain a yellow residue.

3-(3,5-bis(trifluoromethyl)benzylamino)propanol (18.5 g) and triethylamine (40 mL) were dissolved in tetrahydrofuran (100 mL). While the solution was chilled on an ice bath, a tetrahydrofuran solution of the yellow residue (80 mL) was added. After stirred for 1 hour, the mixture was further stirred for additional 2 hours at room temperature. The reaction mixture was then diluted with ethyl acetate, was sequentially washed with water, 1 mol/L hydrochloric acid, and a saturated aqueous solution of sodium chloride, and was then dried over anhydrous sodium sulfate. Following removal of the solvent, the resulting brown residue was dissolved in N,N-dimethylformamide (60 mL). To this solution, potassium carbonate (24.3 g) was added and the resulting mixture was stirred at 80° C. for 1 hour. Subsequently, the reaction mixture was allowed to cool, was diluted with ethyl acetate, was sequentially washed with water and a saturated aqueous solution of sodium chloride, and was then dried over anhydrous sodium sulfate. Following removal of the solvent, the residue was purified on a silica gel column chromatography (ethyl acetate:hexane=1:1) to obtain 5-[3,5-bis(trifluoromethyl)benzyl]-7-chloro-9-(methylthio)-6-oxo-2,3,4,5-tetrahydro-6H-pyrimido[4,5-b][1,5]oxazocine (17.8 g, 63%).

MS(EI)m/z: 485(M+) HRMS(EI): Calcd for $C_{18}H_{14}ClF_6N_3O_2S$: 485.0399; found: 485.0358.

Reference Example 10

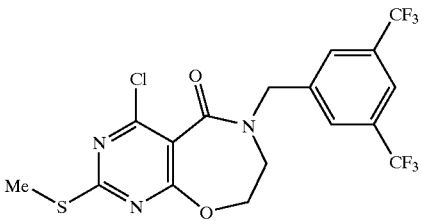

In a similar manner to Reference Example 9, 4,6-dichloro-2-(methylthio)pyrimidine-5-carboxylic acid (Compound of Reference Example 4; 5.00 g) was reacted with 2-(3,5-bis(trifluoromethyl)benzylamino)ethanol (prepared according to the method described in Japanese Patent Laid-Open Publication No. Hei 9-263585; 6.30 g) to obtain 4-[3,5-bis(trifluoromethyl)benzyl]-6-chloro-8-(methylthio)-5-oxo-2,3,4,5-tetrahydropyrimido[5,4-f][1,4]oxazepine (5.15 g, 52%).

MS(EI)m/z: 471(M+) HRMS(EI): Calcd for $C_{17}H_{12}ClF_6N_3O_2S$: 471.0243; found: 471.0236.

Reference Example 11

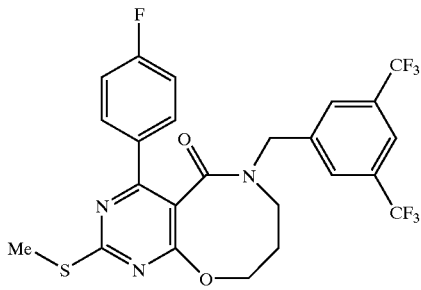

4-fluorophenylboronic acid (387 mg), tetrakis(triphenylphosphine)palladium (133 mg), toluene(10 mL), 1,4-dioxane(5 mL), and a 2 mol/L aqueous solution of sodium carbonate (10 mL) were added to 5-[3,5-bis(trifluoromethyl)benzyl]-7-chloro-9-(methylthio)-6-oxo-2,3,4,5-tetrahydro-6H-pyrimido[4,5-b][1,5]oxazocine (Compound of Reference Example 9; 1.12 g). While heated, the resulting mixture was refluxed for 6 hours under a stream of argon gas. Subsequently, the reaction mixture was diluted with ethyl acetate, was washed with a 2 mol/L aqueous solution of sodium carbonate, and was then dried over anhydrous sodium sulfate. The solvent was removed and the resulting residue was purified on a silica gel column chromatography (ethyl acetate:hexane=1:1) to obtain 5-[3,5-bis(trifluoromethyl)benzyl]-7-(4-fluorophenyl)-9-(methylthio)-6-oxo-2,3,4,5-tetrahydro-6H-pyrimido[4,5-b][1,5]oxazocine (1.22 g, 97%).

MS(EI)m/z: 545(M+) HRMS(EI): Calcd for $C_{24}H_{18}F_7N_3O_2S$: 545.1008; found: 545.1017.

Reference Example 12

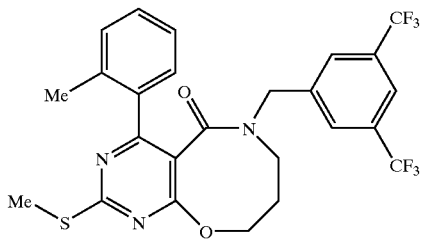

In a similar manner to Reference Example 11, 5-[3,5-bis(trifluoromethyl)benzyl]-7-chloro-9-(methylthio)-6-oxo-2,3,4,5-tetrahydro-6H-pyrimido[4,5-b][1,5]oxazocine (Compound of Reference-Example 9; 4.86 g) was reacted with 2-methylphenylboronic acid (1.64 g) to obtain 5-[3,5-bis(trifluoromethyl)benzyl]-7-(2-methylphenyl)-9-(methylthio)-6-oxo-2,3,4,5-tetrahydro-6H-pyrimido[4,5-b][1,5]oxazocine (5.12 g, 95%).

MS(EI)m/z: 541(M+) HRMS(EI): Calcd for $C_{25}H_{21}F_6N_3O_2S$: 541.1259; found: 541.1241.

Reference Example 13

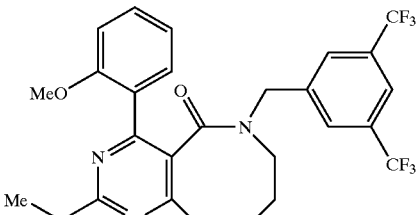

In a similar manner to Reference Example 11, 5-[3,5-bis(trifluoromethyl)benzyl]-7-chloro-9-(methylthio)-6-oxo-2,3,4,5-tetrahydro-6H-pyrimido[4,5-b][1,5]oxazocine (Compound of Reference Example 9; 1.95 g) was reacted with 2-methoxyphenylboronic acid (730 mg) to obtain 5-[3,5-bis(trifluoromethyl)benzyl]-7-(2-methoxyphenyl)-9-(methylthio)-6-oxo-2,3,4,5-tetrahydro-6H-pyrimido[4,5-b][1,5]oxazocine (1.96 g, 88%).

MS(EI)m/z: 557(M+) HRMS(EI): Calcd for $C_{25}H_{21}F_6N_3O_3S$: 557.1208; found: 557.1216.

Reference Example 14

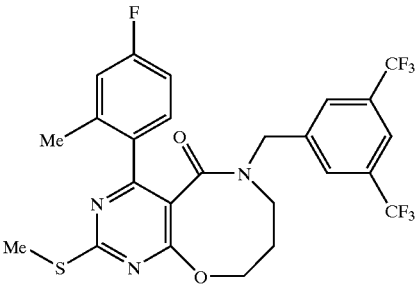

In a similar manner to Reference Example 11, 5-[3,5-bis(trifluoromethyl)benzyl]-7-chloro-9-(methylthio)-6-oxo-2,3,4,5-tetrahydro-6H-pyrimido[4,5-b][1,5]oxazocine (Compound of Reference Example 9; 1.22 g) was reacted with 4-fluoro-2-methylphenylboronic acid (464 mg) to obtain 5-[3,5-bis(trifluoromethyl)benzyl]-7-(4-fluoro-2-methylphenyl)-9-(methylthio)-6-oxo-2,3,4,5-tetrahydro-6H-pyrimido[4,5-b][1,5]oxazocine (1.35 g, 96%).

MS(EI)m/z: 559(M+) HRMS(EI): Calcd for $C_{25}H_{20}F_7N_3O_2S$: 559.1164; found: 559.1176.

Reference Example 15

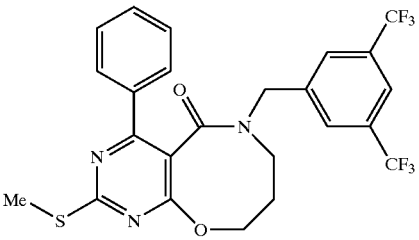

In a similar manner to Reference Example 11, 5-[3,5-bis (trifluoromethyl)benzyl]-7-chloro-9-(methylthio)-6-oxo-2,3,4,5-tetrahydro-6H-pyrimido[4,5-b][1,5]oxazocine (Compound of Reference Example 9; 2.43 g) was reacted with phenylboronic acid (732 mg) to obtain 5-[3,5-bis(trifluoromethyl)benzyl]-7-phenyl-9-(methylthio)-6-oxo-2,3,4,5-tetrahydro-6H-pyrimido[4,5-b][1,5]oxazocine (2.28 g, 86%).

MS(EI)m/z: 527($M^+$) HRMS(EI): Calcd for $C_{24}H_{19}F_6N_3O_2S$: 527.1102; found: 527.1130.

Reference Example 16

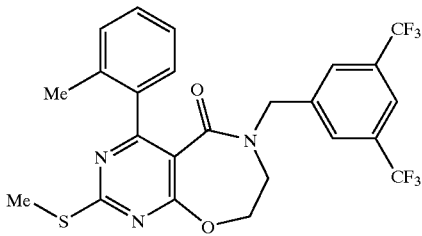

In a similar manner to Reference Example 11, 4-[3,5-bis (trifluoromethyl)benzyl]-6-chloro-8-(methylthio)-5-oxo-2,3,4,5-tetrahydropyrimido[5,4-f][1,4]oxazepine (Compound of Reference Example 10; 2.36 g) was reacted with 2-methylphenylboronic acid (816 mg) to obtain 4-[3,5-bis(trifluoromethyl)benzyl]-6-(2-methylphenyl)-8-(methylthio)-5-oxo-2,3,4,5-tetrahydropyrimido[5,4-f][1,4]oxazepine (2.13 g, 81%).

MS(EI)m/z: 527($M^+$) HRMS(EI): Calcd for $C_{24}H_{19}F_6N_3O_2S$: 527.1102; found: 527.1130.

Reference Example 17

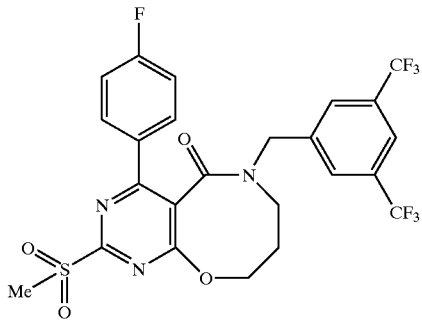

5-[3,5-bis(trifluoromethyl)benzyl]-7-(4-fluorophenyl)-9-(methylthio)-6-oxo-2,3,4,5-tetrahydro-6H-pyrimido[4,5-b][1,5]oxazocine (Compound of Reference Example 11; 1.15 g) was dissolved in tetrahydrofuran (6 mL). While the solution was chilled on an ice bath, 3-chloroperbenzoic acid (1.09 g) was added and the mixture was stirred at room temperature for 3 hours. Subsequently, the reaction mixture was diluted with ethyl acetate, was washed with saturated sodium hydrogen carbonate, and was then dried over anhydrous sodium sulfate. The solvent was removed and the resulting residue was purified on a silica gel column chromatography (ethyl acetate:hexane=2:1) to obtain 5-[3,5-bis(trifluoromethyl)benzyl]-7-(4-fluorophenyl)-9-(methylsulfonyl)-6-oxo-2,3,4,5-tetrahydro-6H-pyrimido[4,5-b][1,5]oxazocine (990 mg, 81%).

MS(EI)m/z: 577($M^+$) HRMS(EI): Calcd for $C_{24}H_{18}F_7N_3O_4S$: 577.0906; found: 577.0898.

Reference Example 18

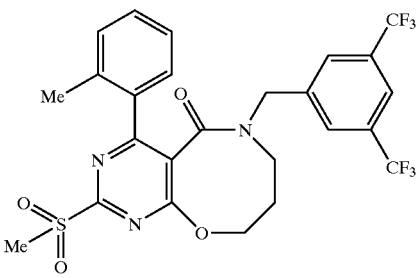

In a similar manner to Reference Example 17, 5-[3,5-bis (trifluoromethyl)benzyl]-7-(2-methylphenyl)-9-(methylthio)-6-oxo-2,3,4,5-tetrahydro-6H-pyrimido[4,5-b][1,5]oxazocine (Compound of Reference Example 12; 4.50 g) was used to obtain 5-[3,5-bis(trifluoromethyl)benzyl]-7-(2-methylphenyl)-9-(methylsulfonyl)-6-oxo-2,3,4,5-tetrahydro-6H-pyrimido[4,5-b][1,5]oxazocine (4.98 g, 100%).

MS(EI)m/z: 573($M^+$) HRMS(EI): Calcd for $C_{25}H_{21}F_6N_3O_4S$: 573.1157; found: 573.1144.

Reference Example 19

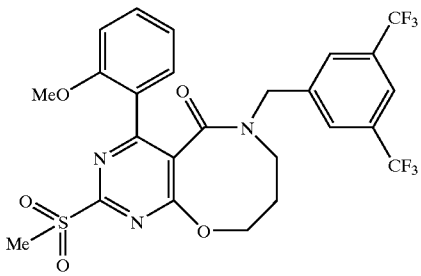

In a similar manner to Reference Example 17, 5-[3,5-bis (trifluoromethyl)benzyl]-7-(2-methoxyphenyl)-9-(methylthio)-6-oxo-2,3,4,5-tetrahydro-6H-pyrimido[4,5-b][1,5]oxazocine (Compound of Reference Example 13; 1.80 g) was used to obtain 5-[3,5-bis(trifluoromethyl)benzyl]-7-(2-methoxyphenyl)-9-(methylsulfonyl)-6-oxo-2,3,4,5-tetrahydro-6H-pyrimido[4,5-b][1,5]oxazocine (1.75 g, 85%).

MS(EI)m/z: 589($M^+$) HRMS(EI): Calcd for $C_{25}H_{21}F_6N_3O_5S$: 589.1106; found: 589.1082.

Reference Example 20

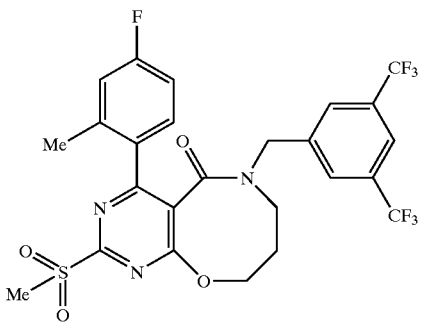

In a similar manner to Reference Example 17, 5-[3,5-bis(trifluoromethyl)benzyl]-7-(4-fluoro-2-methylphenyl)-9-(methylthio)-6-oxo-2,3,4,5-tetrahydro-6H-pyrimido[4,5-b][1,5]oxazocine (Compound of Reference Example 14; 1.22 g) was used to obtain 5-[3,5-bis(trifluoromethyl)benzyl]-7-(4-fluoro-2-methylphenyl)-9-(methylsulfonyl)-6-oxo-2,3,4,5-tetrahydro-6H-pyrimido[4,5-b][1,5]oxazocine (1.29 g, 100%).

MS(EI)m/z: 591(M⁺) HRMS(EI): Calcd for $C_{25}H_{20}F_7N_3O_4S$: 591.1063; found: 591.1063.

Reference Example 21

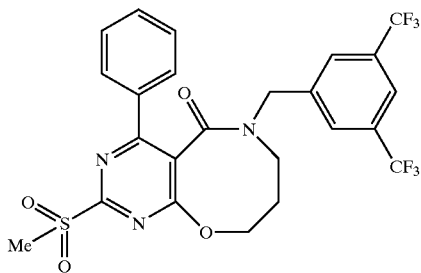

In a similar manner to Reference Example 17, 5-[3,5-bis(trifluoromethyl)benzyl]-9-(methylthio)-6-oxo-7-phenyl-2,3,4,5-tetrahydro-6H-pyrimido[4,5-b][1,5]oxazocine (Compound of Reference Example 15; 2.15 g) was used to obtain 5-[3,5-bis(trifluoromethyl)benzyl]-9-(methylsulfonyl)-6-oxo-7-phenyl-2,3,4,5-tetrahydro-6H-pyrimido[4,5-b][1,5]oxazocine (1.77 g, 78%).

MS(EI)m/z: 559 (M⁺) HRMS(EI): Calcd for $C_{24}H_{19}F_6N_3O_4S$: 559.1000; found: 559.0974.

Reference Example 22

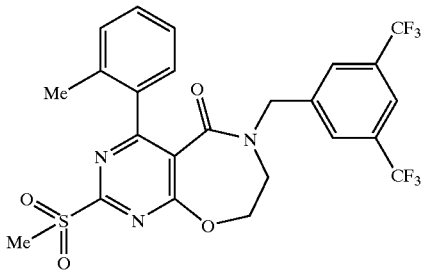

In a similar manner to Reference Example 17, 4-[3,5-bis(trifluoromethyl)benzyl]-6-(methylphenyl)-8-(methylthio)-5-oxo-2,3,4,5-tetrahydropyrimido[5,4-f][1,4]oxazepine (Compound of Reference Example 16; 1.95 g) was used to obtain 4-[3,5-bis(trifluoromethyl)benzyl]-6-(2-methylphenyl)-8-(methylsulfonyl)-5-oxo-2,3,4,5-tetrahydropyrimido[5,4-f][1,4]oxazepine (1.73 g, 84%).

MS(EI)m/z: 559(M⁺) HRMS(EI): Calcd for $C_{24}H_{19}F_6N_3O_4S$: 559.1000; found: 559.1016

Reference Example 23

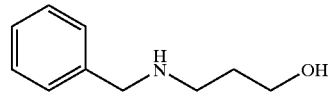

3-amino-1-propanol (150 g) was dissolved in tetrahydrofuran (200 mL), followed by the addition of benzylamine (23.8 g). The mixture was stirred at room temperature for 1 hour. Subsequently, the reaction mixture was diluted with ethyl acetate, was sequentially washed with water and a saturated aqueous solution of sodium chloride, and was then dried over anhydrous sodium sulfate. The solvent was removed to obtain 3-(benzylamino)-1-propanol (20.1 g, 61%).

MS(EI)m/z: 165 (M⁺)

Reference Example 24

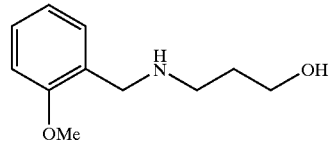

In a similar manner to Reference Example 23, 3-amino-1-propanol (27.0 g) was reacted with 2-methoxybenzylchloride (5.00 g) to obtain 3-(2-methoxybenzylamino)-1-propanol (3.48 g, 50%).

MS(EI)m/z: 195 (M⁺)

Reference Example 25

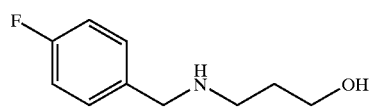

In a similar manner to Reference Example 23, 3-amino-1-propanol (52.0 g) was reacted with 4-fluorobenzylchloride (10.0 g) to obtain 3-(4-fluorobenzylamino)-1-propanol (8.10 g, 64%).

MS(EI)m/z: 183 (M⁺)

Reference Example 26

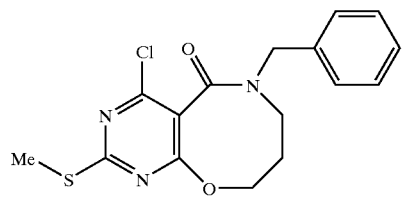

In a similar manner to Reference Example 9, 4,6-dichloro-2-(methylthio)pyrimidine-5-carboxylic acid (Compound of Reference Example 4; 600 mg) was reacted with 3-(benzylamino)propanol (Compound of Reference Example 23; 500 mg) to obtain 5-benzyl-7-chloro-9-(methylthio)-6-oxo-2,3,4,5-tetrahydro-6H-pyrimido[4,5-b][1,5]oxazocine (274 mg, 31%).

MS(EI)m/z: 349(M$^+$) HRMS(EI): Calcd for $C_{16}H_{16}ClN_3O_2S$: 349.0652; found: 349.0636.

Reference Example 27

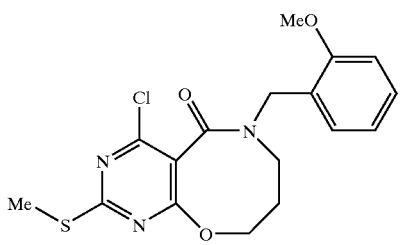

In a similar manner to Reference Example 9, 4,6-dichloro-2-(methylthio)pyrimidine-5-carboxylic acid (Compound of Reference Example 4; 600 mg) was reacted with 3-(2-methoxybenzylamino)propanol (Compound of Reference Example 24; 589 mg) to obtain 7-chloro-5-(2-methoxybenzyl)-9-(methylthio)-6-oxo-2,3,4,5-tetrahydro-6H-pyrimido[4,5-b][1,5]oxazocine (213 mg, 22%).

MS(EI)m/z: 379(M$^+$) HRMS(EI): Calcd for $C_{17}H_{18}ClN_3O_3S$: 379.0757; found: 379.0779.

Reference Example 28

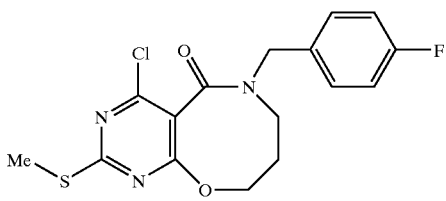

In a similar manner to Reference Example 9, 4,6-dichloro-2-(methylthio)pyrimidine-5-carboxylic acid (Compound of Reference Example 4; 600 mg) was reacted with 3-(4-fluorobenzylamino)propanol (Compound of Reference Example 25; 554 mg) to obtain 7-chloro-5-(4-fluorobenzyl)-9-(methylthio)-6-oxo-2,3,4,5-tetrahydro-6H-pyrimido[4,5-b][1,5]oxazocine (284 mg, 31%).

MS(EI)m/z: 367(M$^+$) HRMS(EI): Calcd for $C_{16}H_{15}ClFN_3O_2S$: 367.0558; found: 367.0541.

Reference Example 29

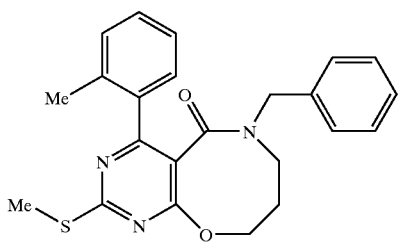

In a similar manner to Reference Example 11, 5-benzyl-7-chloro-9-(methylthio)-6-oxo-2,3,4,5-tetrahydro-6H-pyrimido[4,5-b][1,5]oxazocine (Compound of Reference Example 26; 245 mg) was reacted with 2-methylphenylboronic acid (115 mg) to obtain 5-benzyl-7-(2-methylphenyl)-9-(methylthio)-6-oxo-2,3,4,5-tetrahydro-6H-pyrimido[4,5-b][1,5]oxazocine (230 mg, 81%).

MS(FAB$^+$) m/z: 406(M+H$^+$) HRMS(FAB$^+$): Calcd for $C_{23}H_{24}N_3O_2S$: 406.1589; found: 406.1599.

Reference Example 30

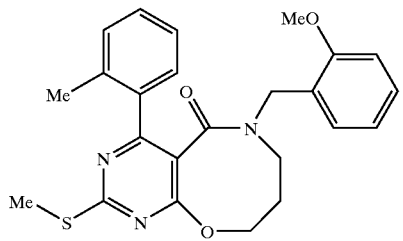

In a similar manner to Reference Example 11, 7-chloro-5-(2-methoxybenzyl)-9-(methylthio)-6-oxo-2,3,4,5-tetrahydro-6H-pyrimido[4,5-b][1,5]oxazocine (Compound of Reference Example 27; 197 mg) was reacted with 2-methylphenylboronic acid (85.0 mg) to obtain 5-(2-methoxybenzyl)-7-(2-methylphenyl)-9-(methylthio)-6-oxo-2,3,4,5-tetrahydro-6H-pyrimido[4,5-b][1,5]oxazocine (212 mg, 94%).

MS(FAB$^+$) m/z: 436(M+H$^+$) HRMS(FAB$^+$): Calcd for $C_{24}H_{26}N_3O_3S$: 436.1695; found: 436.1694.

Reference Example 31

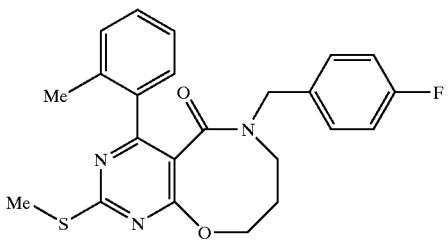

In a similar manner to Reference Example 11, 7-chloro-5-(4-fluorobenzyl)-9-(methylthio)-6-oxo-2,3,4,5-tetrahydro-6H-pyrimido[4,5-b][1,5]oxazocine (Compound of Reference Example 28; 231 mg) was reacted with 2-methylphenylboronic acid (103 mg) to obtain 5-(4-fluorobenzyl)-7-(2-methylphenyl)-9-(methylthio)-6-oxo-2,3,4,5-tetrahydro-6H-pyrimido[4,5-b][1,5]oxazocine (257 mg, 97%).

MS(FAB$^+$) m/z: 424 (M+H$^+$) HRMS(FAB$^+$): Calcd for $C_{23}H_{23}FN_3O_2S$: 424.1495; found: 424.1504.

Reference Example 32

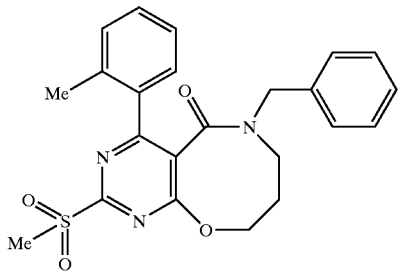

In a similar manner to Reference Example 17, 5-benzyl-7-(2-methylphenyl)-9-(methylthio)-6-oxo-2,3,4,5-tetrahydro-6H-pyrimido[4,5-b][1,5]oxazocine (Compound of Reference Example 29; 215 mg) was used to obtain 5-benzyl-7-(2-methylphenyl)-9-(methylsulfonyl)-6-oxo-2,3,4,5-tetrahydro-6H-pyrimido[4,5-b][1,5]oxazocine (210 mg, 91%).

MS(FAB$^+$) m/z: 438 (M+H$^+$) HRMS(FAB$^+$): Calcd for $C_{23}H_{24}N_3O_4S$: 438.1488; found: 438.1461.

Reference Example 33

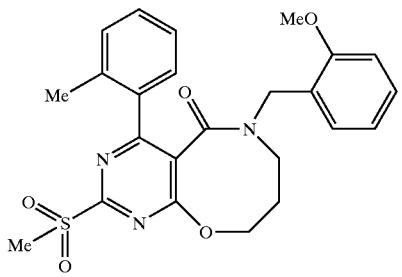

In a similar manner to Reference Example 17, 5-(2-methoxybenzyl)-7-(2-methylphenyl)-9-(methylthio)-6-oxo-2,3,4,5-tetrahydro-6H-pyrimido[4,5-b][1,5]oxazocine (Compound of Reference Example 30; 202 mg) was used to obtain 5-(2-methoxybenzyl)-7-(2-methylphenyl)-9-(methylsulfonyl)-6-oxo-2,3,4,5-tetrahydro-6H-pyrimido[4.5-b][1,5]oxazocine (188 mg, 87%).

MS(FAB$^+$) m/z: 468 (M+H$^+$) HRMS(FAB$^+$): Calcd for $C_{24}H_{26}N_3O_5S$: 468.1593; found: 468.1583.

Reference Example 34

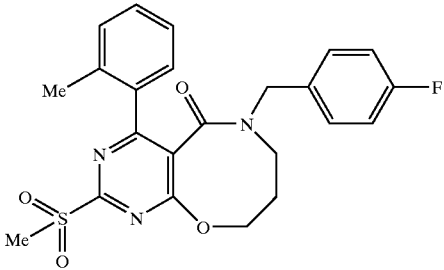

In a similar manner to Reference Example 17, 5-(4-fluorobenzyl)-7-(2-methylphenyl)-9-(methylthio)-6-oxo-2,3,4,5-tetrahydro-6H-pyrimido[4,5-b][1,5]oxazocine (Compound of Reference Example 31; 230 mg) was used to obtain 5-(4-fluorobenzyl)-7-(2-methylphenyl)-9-(methylsulfonyl)-6-oxo-2,3,4,5-tetrahydro-6H-pyrimido[4,5-b][1,5]oxazocine (225 mg, 91%).

MS(FAB$^+$) m/z: 456 (M+H$^+$) HRMS(FAB$^+$): Calcd for $C_{23}H_{23}FN_3O_4S$: 456.1393; found: 456.1413.

Example 1

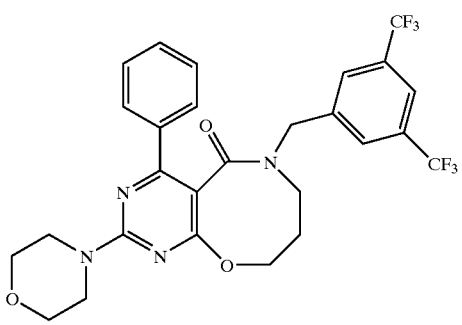

Phenylboronic acid (27.4 mg), tetrakis(triphenylphosphine)palladium (8.8 mg), toluene (1 mL), 1,4-dioxane (0.5 mL), and a 2 mol/L aqueous solution of sodium carbonate (1 mL) were added to 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg). While heated, the mixture was refluxed for 3 hours under a stream of argon gas. Subsequently, the reaction mixture was diluted with ethyl acetate, was washed with a 2 mol/L aqueous solution of sodium carbonate, and was then dried over anhydrous sodium sulfate. The solvent was removed and the resulting residue was purified on a silica gel column chromatography (ethyl acetate:hexane=2:1) to obtain 5-[3,5-bis(trifluoromethyl)benzyl]-9-(morpholine-4-yl)-6-oxo-7-phenyl-2,3,4,5-tetrahydro-6H-pyrimido[4,5-b][1,5]oxazocine (80.9 mg, 95%) in the form of yellow amorphous product.

MS(EI)m/z: 566(M$^+$) HRMS(EI): Calcd for $C_{27}H_{24}F_6N_4O_3$: 566.1753; found: 566.1760.

Example 2

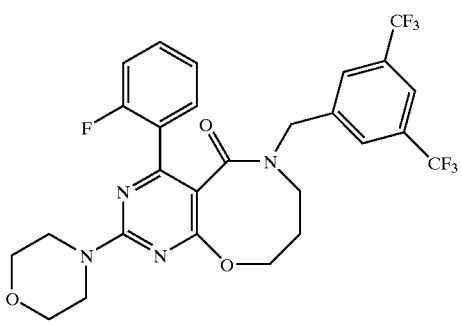

In a similar manner to Example 1, 5-[3,5-bis(trifluoromethyl)benzyl]-7-chloro-9-(morpholine-4-yl)-6-oxo-2,3,4,5- tetrahydro-6H-pyrimido[4,5-b][1,5]oxazocine (Compound of Reference Example 7; 78.8 mg) was reacted with 2-fluorophenylboronic acid (31.5 mg) to obtain 5-[3,5-bis(trifluoromethyl)benzyl]-7-(2-fluorophenyl)-9-(morpholine-4-yl)-6-oxo-2,3,4,5-tetrahydro-6H-pyrimido[4,5-b][1,5]oxazocine (75.6 mg, 86%).

MS(EI)m/z: 584(M$^+$) HRMS(EI): Calcd for $C_{27}H_{23}F_7N_4O_3$: 584.1658; found: 584.1650. $^1$H-NMR (400 Mz, CDCl$_3$)ppm:2.00–2.09(2H, m), 3.29–3.38(1H, m), 3.71–3.78(4H, m), 3.81–3.92(5H, m), 3.99(1H, d, J=15.1 Hz), 4.32–4.45(2H, m), 5.36(1H, d, J=15.1 Hz), 6.92–6.98 (1H, m), 7.16–7.22(1H, m), 7.31–7.37(1H, m), 7.44–7.50 (1H, m), 7.73(2H, s), 7.82(1H, s)

Example 3

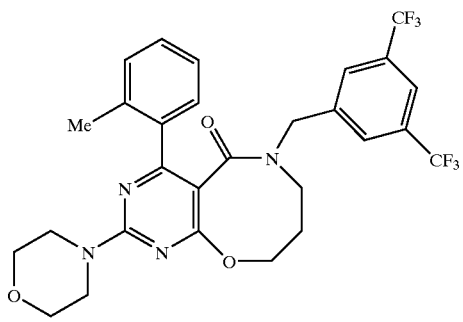

In a similar manner to Example 1, 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg) was reacted with 2-methylphenylboronic acid (30.6 mg) to obtain 5-[3,5-bis(trifluoromethyl)benzyl]-7-(2-methylphenyl)-9-(morpholine-4-yl)-6-oxo-2,3,4,5-tetrahydro-6H-pyrimido[4,5-b][1,5]oxazocine (74.4 mg, 85%).

MS(EI)m/z: 580 (M$^+$) HRMS(EI): Calcd for $C_{28}H_{26}F_6N_4O_3$: 580.1909; found: 580.1948.

Example 4

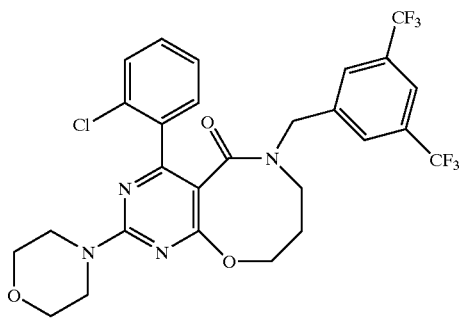

In a similar manner to Example 1, 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg) was reacted with 2-chlorophenylboronic acid (28.1 mg) to obtain 5-[3,5-bis(trifluoromethyl)benzyl]-7-(2-chlorophenyl)-9-(morpholine-4-yl)-6-oxo-2,3,4,5-tetrahydro-6H-pyrimido[4,5-b][1,5]oxazocine (79.0 mg, 88%).

MS(EI)m/z: 600(M$^+$) HRMS(EI): Calcd for $C_{27}H_{23}ClF_6N_4O_3$: 600.1363; found: 600.1375.

Example 5

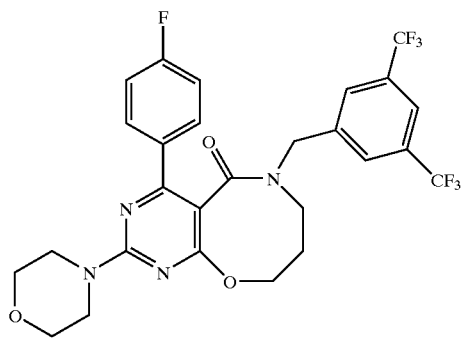

In a similar manner to Example 1, 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg) was reacted with 4-fluorophenylboronic acid (25.2 mg) to obtain 5-[3,5-bis(trifluoromethyl)benzyl]-7-(4-fluorophenyl)-9-(morpholine-4-yl)-6-oxo-2,3,4,5-tetrahydro-6H-pyrimido[4,5-b][1,5]oxazocine (61.5 mg, 70%).

MS(EI)m/z: 584(M$^+$) HRMS(EI): Calcd for $C_{27}H_{23}F_7N_4O_3$: 584.1658; found: 584.1659.

Example 6

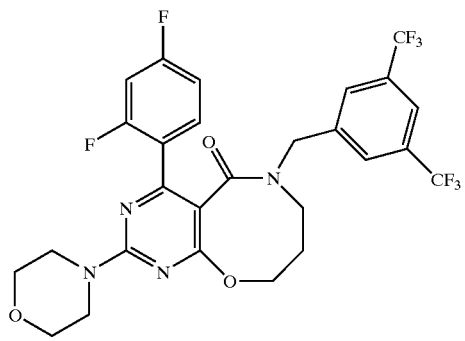

In a similar manner to Example 1, 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg) was reacted with 2,4-difluorophenylboronic acid (28.4 mg) to obtain 5-[3,5-bis(trifluoromethyl)benzyl]-7-(2,4-difluorophenyl)-9-(morpholine-4-yl)-6-oxo-2,3,4,5-tetrahydro-6H-pyrimido[4,5-b][1,5]oxazocine (77.8 mg, 86%).

MS(EI)m/z: 602(M$^+$) HRMS(EI): Calcd for $C_{27}H_{22}F_8N_4O_3$: 602.1564; found: 602.1589.

Example 7

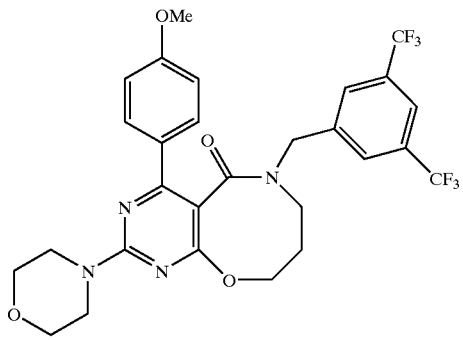

In a similar manner to Example 1, 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg) was reacted with 4-methoxyphenylboronic acid (27.4 mg) to obtain 5-[3,5-bis(trifluoromethyl)benzyl]-7-(4-methoxyphenyl)-9-(morpholine-4-yl)-6-oxo-2,3,4,5-tetrahydro-6H-pyrimido[4,5-b][1,5]oxazocine (72.0 mg, 80%).

MS(EI)m/z: 596(M$^+$) HRMS(EI): Calcd for $C_{28}H_{26}F_6N_4O_4$: 596.1858; found: 596.1871.

Example 8

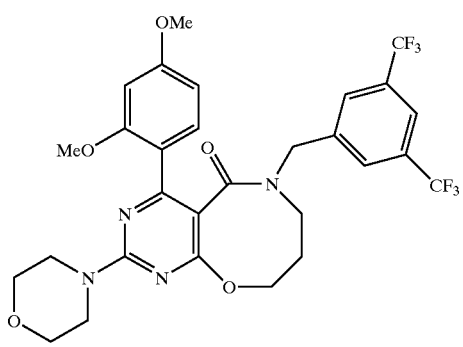

In a similar manner to Example 1, 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg) was reacted with 2,4-dimethoxyphenylboronic acid (32.8 mg) to obtain 5-[3,5-bis(trifluoromethyl)benzyl]-7-(2,4-dimethoxyphenyl)-9-(morpholine-4-yl)-6-oxo-2,3,4,5-tetrahydro-6H-pyrimido[4,5-b][1,5]oxazocine (73.8 mg, 79%).

MS(EI)m/z: 626 (M$^+$) HRMS(EI): Calcd for $C_{29}H_{28}F_6N_4O_5$: 626.1964; found: 626.1951.

Example 9

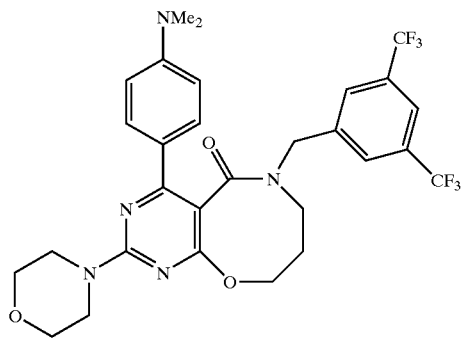

In a similar manner to Example 1, 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg) was reacted with 4-(dimethylamino)phenylboronic acid (29.7 mg) to obtain 5-[3,5-bis(trifluoromethyl)benzyl]-7-[4-(dimethylamino)phenyl]-9-(morpholine-4-yl)-6-oxo-2,3,4,5-tetrahydro-6H-pyrimido[4,5-b][1,5]oxazocine (56.0 mg, 61%).

MS(EI)m/z: 609(M$^+$) HRMS(EI): Calcd for $C_{29}H_{29}F_6N_5O_3$: 609.2175; found: 609.2153.

Example 10

In a similar manner to Example 1, 5-[3,5-bis(trifluoromethyl)benzyl]-7-chloro-9-(morpholine-4-yl)-6-oxo-2,3,4,5-tetrahydro-6H-pyrimido[4,5-b][1,5]oxazocine (Compound of Reference Example 7; 78.8 mg) was reacted with 2-methoxyphenylboronic acid (27.4 mg) to obtain 5-[3,5-bis(trifluoromethyl)benzyl]-7-(2-methoxyphenyl)-9-(morpholine-4-yl)-6-oxo-2,3,4,5-tetrahydro-6H-pyrimido[4,5-b][1,5]oxazocine (77.5 mg, 87%).

MS(EI)m/z: 596(M$^+$) HRMS(EI): Calcd for $C_{28}H_{26}F_6N_4O_4$: 596.1858; found: 596.1843.

Example 11

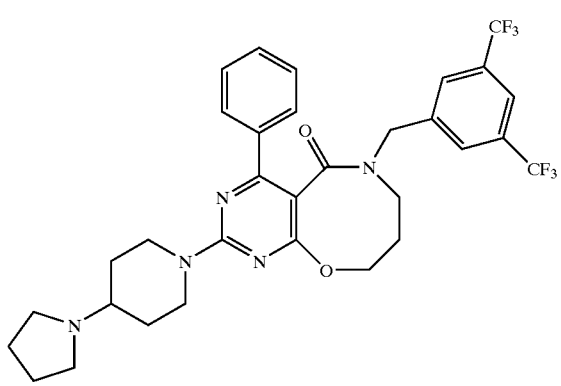

In a similar manner to Example 1, 5-[3,5-bis(trifluoromethyl)benzyl]-7-chloro-6-oxo-9-[4-(pyrrolidine-1-yl)piperidine-1-yl]-2,3,4,5-tetrahydro-6H-pyrimido[4,5-b][1,5]oxazocine (Compound of Reference Example 8; 80.0 mg) was reacted with phenylboronic acid (20.0 mg) to obtain 5-[3,5-bis(trifluoromethyl)benzyl]-6-oxo-7-phenyl-9-[4-(pyrrolidine-1-yl)piperidine-1-yl]-2,3,4,5-tetrahydro-6H-pyrimido[4,5-b][1,5]oxazocine (51.8 mg, 61%).

MS(EI)m/z: 633(M$^+$) HRMS(EI): Calcd for $C_{32}H_{33}F_6N_5O_2$: 633.2538; found: 633.2507.

Example 12

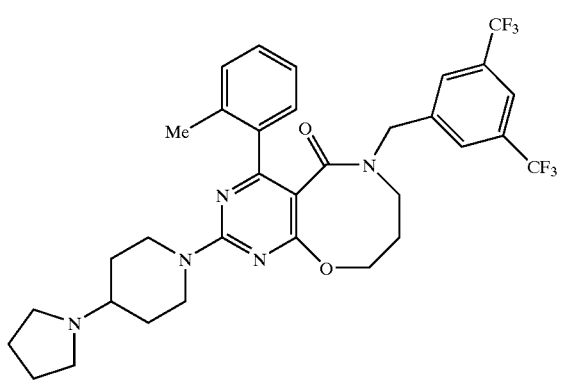

In a similar manner to Example 1, 5-[3,5-bis(trifluoromethyl)benzyl]-7-chloro-6-oxo-9-[4-(pyrrolidine-1-yl)piperidine-1-yl]-2,3,4,5-tetrahydro-6H-pyrimido[4,5-b][1,5]oxazocine (Compound of Reference Example 8; 80.0 mg) was reacted with 2-methylphenylboronic acid (22.0 mg) to obtain 5-[3,5-bis(trifluoromethyl)benzyl]-7-(2-methylphenyl)-6-oxo-9-[4-(pyrrolidine-1-yl)piperidine-1-yl]-2,3,4,5-tetrahydro-6H-pyrimido[4,5-b][1,5]oxazocine (45.0 mg, 51%).

MS(EI)m/z: 647(M$^+$) HRMS(EI): Calcd for $C_{33}H_{35}F_6N_5O_2$: 647.2695; found: 647.2707.

Example 13

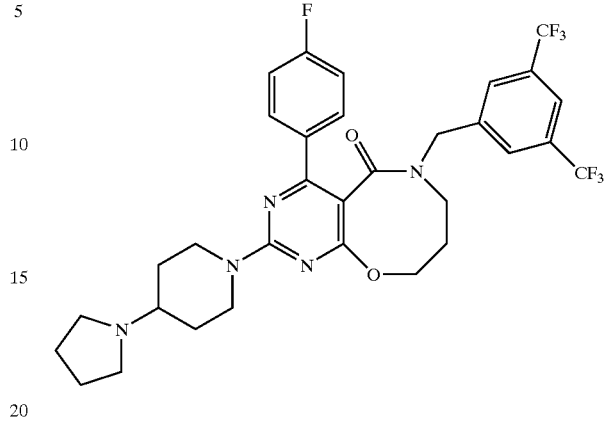

4-(pyrrolidine-1-yl)piperidine (268 mg), diisopropylethylamine (0.6 mL), and 1,4-dioxane (10 mL) were added to 5-[3,5-bis(trifluoromethyl)benzyl]-7-(4-fluorophenyl)-9-(methylsulfonyl)-6-oxo-2,3,4,5-tetrahydro-6H-pyrimido[4,5-b][1,5]oxazocine (Compound of Reference Example 17; 914 mg). The mixture was refluxed for 5 hours while heated. Following removal of the solvent under reduced pressure, the resulting residue was diluted with ethyl acetate, was sequentially washed with a saturated aqueous solution of sodium hydrogen carbonate and a saturated aqueous solution of sodium chloride, and was then dried over anhydrous sodium sulfate. The solvent was removed and the resulting residue was purified on a silica gel column chromatography (ethyl acetate:methanol=5:1) to obtain 5-[3,5-bis(trifluoromethyl)benzyl]-7-(4-fluorophenyl)-6-oxo-9-[4-(pyrrolidine-1-yl)piperidine-1-yl]-2,3,4,5-tetrahydro-6H-pyrimido[4,5-b][1,5]oxazocine (631 mg, 61%).

MS(EI)m/z: 651(M$^+$) HRMS(EI): Calcd for $C_{32}H_{32}F_7N_5O_2$: 651.2444; found: 651.2398. $^1$H-NMR(400 Mz, CDCl$_3$)ppm:1.46–1.87(6H, m), 1.92–2.17(4H, m), 2.24–2.36(1H, m), 2.56–2.69(4H, m), 2.99(2H, dd, J=13.2 and 13.2 Hz), 3.39–3.48(1H, m), 3.90–3.99(1H, m), 4.05 (1H, d, J=15.1 Hz), 4.31–4.38(2H, m), 4.67–4.81(2H, m), 5.33(1H, d, J=15.1 Hz), 6.90–6.98(2H, m), 7.39–7.45(2H, m), 7.76(2H, s), 7.86(1H, s)

Example 14

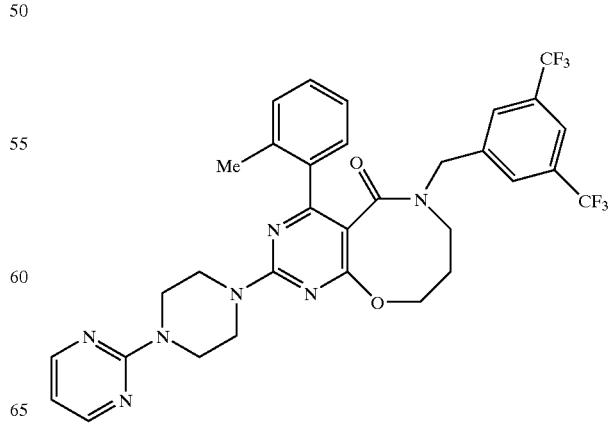

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 1-(pyrimidine-2-yl)piperazine dihydrochloride (43.0 mg) to obtain 5-[3,5-bis(trifluoromethyl)benzyl]-7-(2-methylphenyl)-6-oxo-9-[4-(pyrimidine-2-yl)piperazine-1-yl]-2,3,4,5-tetrahydro-6H-pyrimido[4,5-b][1,5]oxazocine (56.2 mg, 57%).

MS(EI)m/z: 657(M$^+$) HRMS(EI): Calcd for $C_{32}H_{29}F_6N_7O_2$: 657.2287; found: 657.2283. $^1$H-NMR(400 Mz, CDCl$_3$)ppm:1.93–2.03(1H, m), 2.09–2.21(1H, m), 2.27 (3H, s), 3.29(1H, dd, J=15.1 and 4.4 Hz), 3.79–4.00(10H, m), 4.31–4.44(2H, m), 5.33(1H, d, J=15.1 Hz), 6.52(1H, t, J=4.6 Hz), 6.95–7.03(1H, m), 7.03–7.09(1H, m), 7.21–7.26 (2H, m), 7.57(2H, s), 7.80(1H, s), 8.33(2H, d, J=4.6 Hz)

Example 15

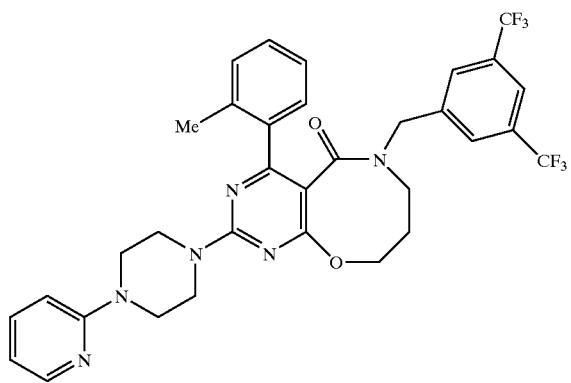

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 1-(pyridine-2-yl)piperazine(30.0 mg) to obtain 5-[3,5-bis(trifluoromethyl)benzyl]-7-(2-methylphenyl)-6-oxo-9-[4-(pyridine-2-yl)piperazine-1-yl]-2,3,4,5-tetrahydro-6H-pyrimido[4,5-b][1,5]oxazocine (77.1 mg, 78%).

MS(EI)m/z: 656(M$^+$) HRMS(EI): Calcd for $C_{33}H_{30}F_6N_6O_2$: 656.2334; found: 656.2310.

Example 16

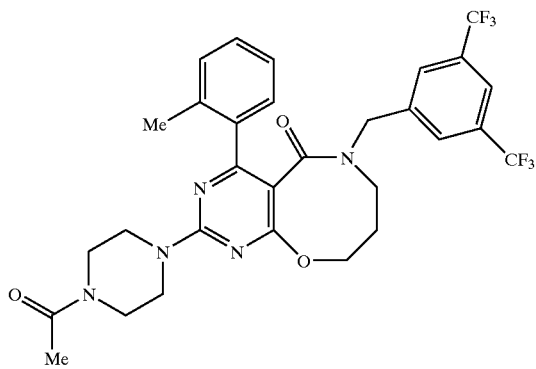

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 1-acetylpiperazine(23.1 mg) to obtain 9-(4-acetylpiperazine-1-yl)-5-[3,5-bis(trifluoromethyl)benzyl]-7-(2-methylphenyl)-6-oxo-2,3,4,5-tetrahydro-6H-pyrimido[4,5-b][1,5]oxazocine (60.7 mg, 65%).

MS(EI)m/z: 621(M$^+$) HRMS(EI): Calcd for $C_{30}H_{29}F_6N_5O_3$: 621.2175; found: 621.2192. $^1$H-NMR(400 Mz, CDCl$_3$)ppm:1.92–2.04(1H, m), 2.10–2.20(1H, m), 2.13 (3H, s), 2.25(3H, s), 3.30(1H, dd, J=15.1 and 4.4 Hz), 3.50(2H, dd, J=4.4 and 4.4 Hz), 3.63–3.70(2H, m), 3.76–3.95(6H, m), 4.30–4.43(2H, m), 5.32(1H, d, J=15.1 Hz), 6.95(1H, brd, J=7.3 Hz), 7.05(1H, brdd, J=7.3 and 7.3 Hz), 7.20–7.25(2H, m), 7.57(2H, s), 7.81(1H, s) Melting point: 160.5–163.5° C.

Element analysis: Calcd for $C_{30}H_{29}F_6N_5O_3$: C, 57.97; H, 4.70; N, 11.27; found: C, 57.90; H, 4.70; N, 11.33.

Example 17

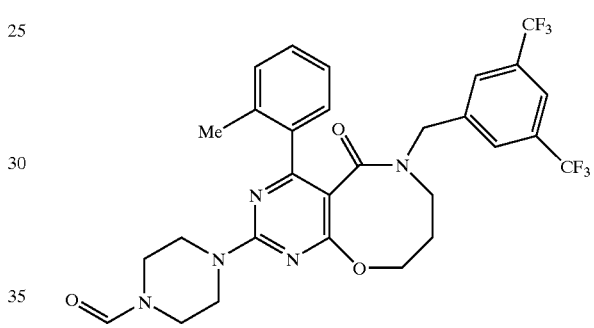

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 1-formylpiperazine (20.6 mg) to obtain 5-[3,5-bis(trifluoromethyl)benzyl]-9-(4-formylpiperazine-1-yl)-7-(2-methylphenyl)-6-oxo-2,3,4,5-tetrahydro-6H-pyrimido[4,5-b][1,5]oxazocine (8.0 mg, 9%).

MS(EI)m/z: 607(M$^+$) HRMS(EI): Calcd for $C_{29}H_{27}F_6N_5O_3$: 607.2018; found: 607.1995.

Example 18

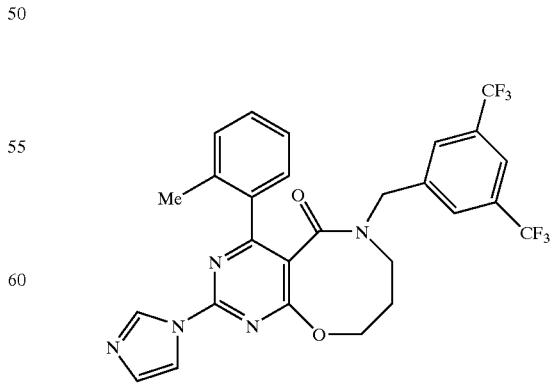

In a similar manner to Example 13, 5-[3,5-bis(trifluoromethyl)benzyl]-9-(methylsulfonyl)-7-(2-methylphenyl)-6- oxo-2,3,4,5-tetrahydro-6H-pyrimido[4,5-b][1,5]oxazocine (Compound of Reference Example 18; 86.0 mg) was reacted with sodium imidazole (16.5 mg) to obtain 5-[3,5-bis(trifluoromethyl)benzyl]-9-(imidazole-1-yl)-7-(2-methylphenyl)-6-oxo-2,3,4,5-tetrahydro-6H-pyrimido[4,5-b][1,5]oxazocine (53.8 mg, 64%).

MS(EI)m/z: 561(M⁺) HRMS(EI): Calcd for $C_{27}H_{21}F_6N_5O_2$: 561.1599; found: 561.1597. ¹H-NMR(400 Mz, CDCl₃)ppm: 2.01–2.12(1H, m), 2.21–2.32(4H, m), 3.41(1H, dd, J=15.6 and 4.9 Hz), 3.74–3.85(1H, m), 3.91 (1H, d, J=14.6 Hz), 4.45–4.57(2H, m), 5.32(1H, d, J=14.6 Hz), 6.94(1H, d, J=7.8 Hz), 7.07(1H, dd, J=7.8 and 7.8 Hz), 7.14(1H, d, J=1.0 Hz), 7.27–7.33(2H, m), 7.59(2H, s), 7.84(1H, s), 7.86(1H, d, J=1.0 Hz), 8.58(1H, s)

Example 19

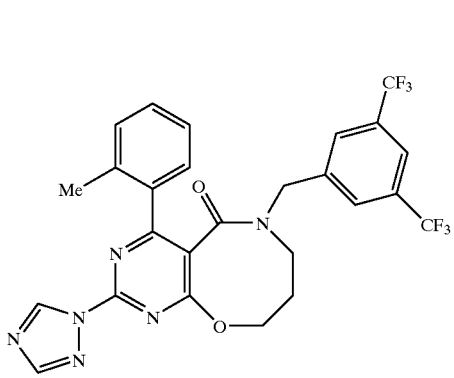

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with a sodium salt of 1,2,4-tetrazole (16.5 mg) to obtain 5-[3,5-bis(trifluoromethyl)benzyl]-7-(2-methylphenyl)-6-oxo-9-(1,2,4-tetrazole-1-yl)-2,3,4,5-tetrahydro-6H-pyrimido[4,5-b][1,5]oxazocine (61.8 mg, 73%).

MS(EI)m/z: 562(M⁺) HRMS(EI): Calcd for $C_{26}H_{20}F_6N_6O_2$:562.1552; found: 562.1569.

Example 20

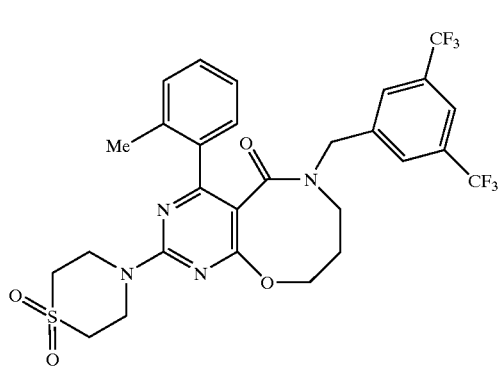

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 1,1-dioxothiomorpholine (24.5 mg) to obtain 5-[3,5-bis(trifluoromethyl)benzyl]-9-(1,1-dioxothiomorpholine-4-yl)-7-(2-methylphenyl)-6-oxo-2,3,4,5-tetrahydro-6H-pyrimido[4,5-b][1,5]oxazocine (12.5 mg, 13%).

MS(EI)m/z: 628(M⁺) HRMS(EI): Calcd for $C_{28}H_{26}F_6N_4O_4S$: 628.1579; found: 628.1523. ¹H-NMR(400 Mz, CDCl₃)ppm:1.94–2.05(1H, m), 2.11–2.21(1H, m), 2.23 (3H, s), 3.00–3.09(4H, m), 3.29–3.37(1H, m), 3.75–3.83 (1H, m), 3.86(1H, d, J=14.6 Hz), 4.33–4.44(6H, m), 5.31 (1H, d, J=14.6 Hz), 6.93(1H, d, J=6.8 Hz), 7.06(1H, dd, J=6.8 and 6.8 Hz), 7.21–7.30(2H, m), 7.57(2H, s), 7.81(1H, s)

Example 21

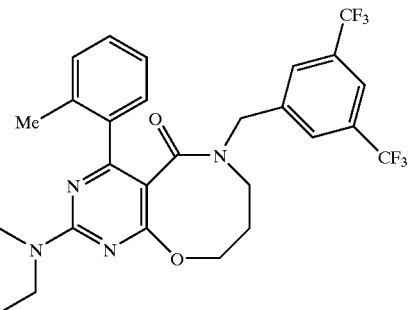

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 3-(ethoxycarbonyl)piperidine (28.3 mg) to obtain 5-[3,5-bis(trifluoromethyl)benzyl]-9-[3-(ethoxycarbonyl)piperidine-1-yl]-7-(2-methylphenyl)-6-oxo-2,3,4,5-tetrahydro-6H-pyrimido[4,5-b][1,5]oxazocine (61.8 mg, 63%).

MS(EI)m/z: 650(M⁺) HRMS(EI): Calcd for $C_{32}H_{32}F_6N_4O_4$: 650.2328; found: 650.2351.

Example 22

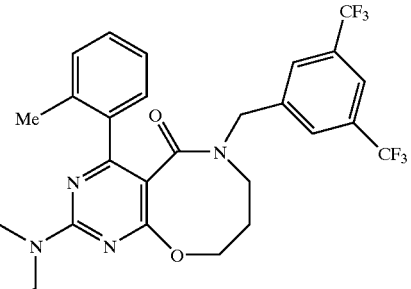

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 4-(ethoxycarbonyl)piperidine (28.3 mg) to obtain 5-[3,5-bis(trifluoromethyl)benzyl]-9-[4-(ethoxycarbonyl)piperidine-1-yl]-7-(2-methylphenyl)-6-oxo-2,3,4,5-tetrahydro-6H-pyrimido[4,5-b][1,5]oxazocine (64.6 mg, 68%).

MS(EI)m/z: 650(M$^+$) HRMS(EI): Calcd for C$_{32}$H$_{32}$F$_6$N$_4$O$_4$: 650.2328; found: 650.2351.

Example 23

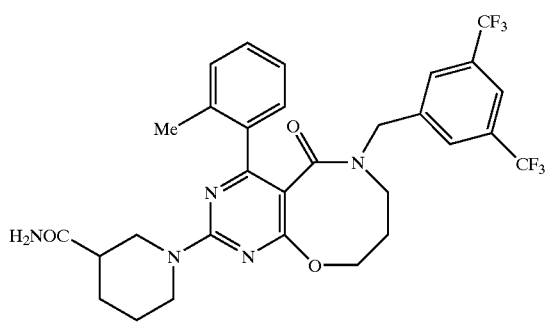

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 3-carbamoylpiperidine (23.1 mg) to obtain 5-[3,5-bis(trifluoromethyl)benzyl]-9-(3-carbamoylpiperidine-1-yl)-7-(2-methylphenyl)-6-oxo-2,3,4,5-tetrahydro-6H-pyrimido[4,5-b][1,5]oxazocine (74.0 mg, 79%).

MS(EI)m/z: 621(M$^+$) HRMS(EI): Calcd for C$_{30}$H$_{29}$F$_6$N$_5$O$_3$: 621.2175; found: 621.2139.

Example 24

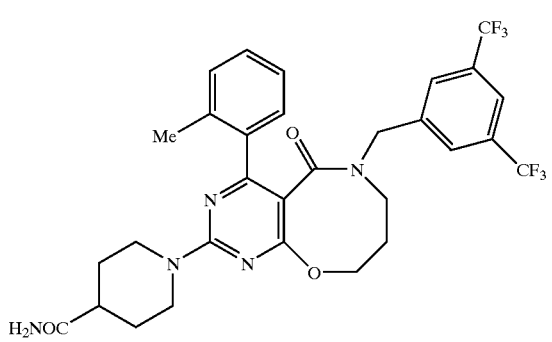

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 4-carbamoylpiperidine (23.1 mg) to obtain 5-[3,5-bis(trifluoromethyl)benzyl]-9-(4-carbamoylpiperidine-1-yl)-7-(2-methylphenyl)-6-oxo-2,3,4,5-tetrahydro-6H-pyrimido[4,5-b][1,5]oxazocine (70.0 mg, 75%).

MS(EI)m/z: 621(M$^+$) HRMS(EI): Calcd for C$_{30}$H$_{29}$F$_6$N$_5$O$_3$: 621.2175; found: 621.2142.

Example 25

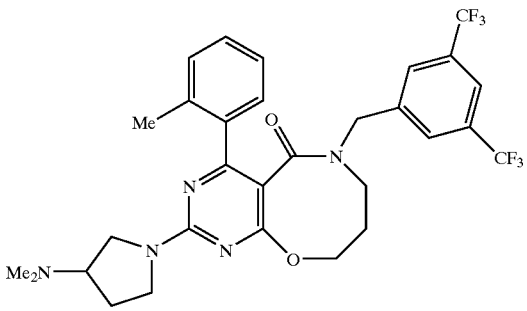

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 3-(dimethylamino)pyrrolidine (20.6 mg) to obtain 5-[3,5-bis(trifluoromethyl)benzyl]-9-[3-(dimethylamino)pyrrolidine-1-yl]-7-(2-methylphenyl)-6-oxo-2,3,4,5-tetrahydro-6H-pyrimido[4,5-b][1,5]oxazocine (54.7 mg, 60%).

MS(EI)m/z: 607(M$^+$) HRMS(EI): Calcd for C$_{30}$H$_{31}$F$_6$N$_5$O$_2$: 607.2382; found: 607.2368.

Example 26

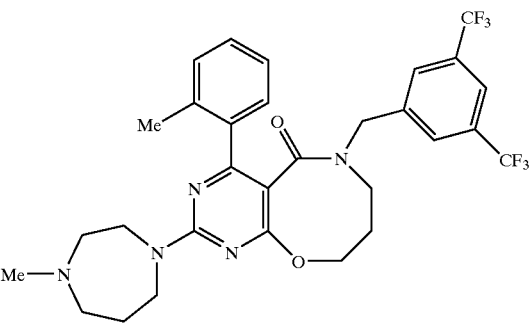

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 1-methylhomopiperazine (20.6 mg) to obtain 5-[3,5-bis(trifluoromethyl)benzyl]-9-(4-methylhomopiperazine-1-yl)-7-(2-methylphenyl)-6-oxo-2,3,4,5-tetrahydro-6H-pyrimido[4,5-b][1,5]oxazocine (55.5 mg, 61%).

MS(EI)m/z: 607(M$^+$) HRMS(EI): Calcd for C$_{30}$H$_{31}$F$_6$N$_5$O$_2$: 607.2382; found: 607.2362.

Example 27

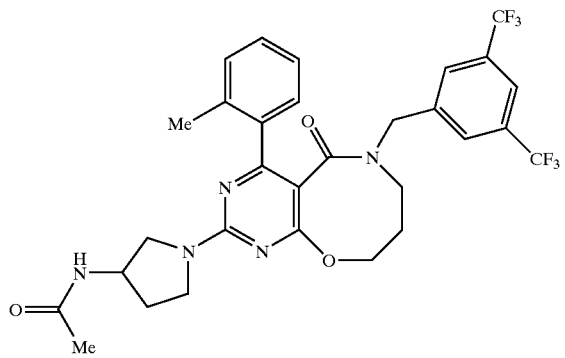

In a similar manner to Example 13, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg) was reacted with 3-(acetylamino)pyrrolidine (23.1 mg) to obtain 5-[3,5-bis(trifluoromethyl)benzyl]-9-[3-(acetylamino)pyrrolidine-1-yl]-7-(2-methylphenyl)-6-oxo-2,3,4,5-tetrahydro-6H-pyrimido[4,5-b][1,5]oxazocine (65.0 mg, 70%).

MS(EI)m/z: 621(M$^+$) HRMS(EI): Calcd for $C_{30}H_{29}F_6N_5O_3$: 621.2175; found: 621.2173. $^1$H-NMR(400 Mz, CDCl$_3$)ppm:1.90–2.03(5H, m), 2.07–2.19(1H, m), 2.19–2.32(4H, m), 3.28(1H, dd, J=15.1 and 4.9 Hz), 3.49 (1H, dd, J=11.7 and 4.4 Hz), 3.69(2H, dd, J=6.8 and 6.8 Hz), 3.74–3.91(3H, m), 4.29–4.42(2H, m), 4.52–4.62(1H, m), 5.32(1H, d, J=14.6 Hz), 5.63(1H, brs), 6.91–6.98(1H, m), 7.01–7.08(1H, m), 7.18–7.26(2H, m), 7.57(2H, s), 7.80(1H, s)

Example 28

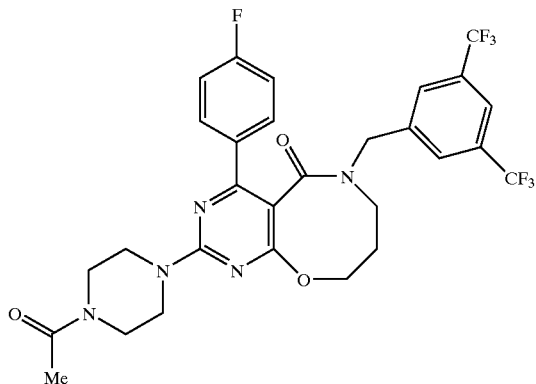

In a similar manner to Example 13, 5-[3,5-bis(trifluoromethyl)benzyl]-7-(4-fluorophenyl)-9-(methylsulfonyl)-6-oxo-2,3,4,5-tetrahydro-6H-pyrimido[4,5-b][1,5]oxazocine (Compound of Reference Example 17; 86.6 mg) was reacted with 1-acetylpiperazine (48.1 mg) to obtain 9-(4-acetylpiperazine-1-yl)-5-[3,5-bis(trifluoromethyl)benzyl]-7-(4-fluorophenyl)-6-oxo-2,3,4,5-tetrahydro-6H-pyrimido[4,5-b][1,5]oxazocine (68.2 mg, 73%).

MS(EI)m/z: 625(M$^+$) HRMS(EI): Calcd for $C_{29}H_{26}F_7N_5O_3$: 625.1924; found: 625.1972.

Example 29

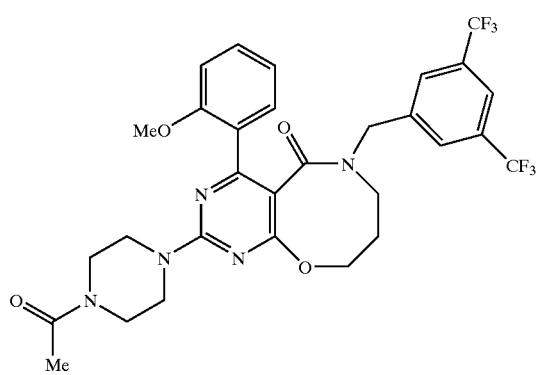

In a similar manner to Example 13, 5-[3,5-bis(trifluoromethyl)benzyl]-9-(methylsulfonyl)-7-(2-methoxyphenyl)-6-oxo-2,3,4,5-tetrahydro-6H-pyrimido[4,5-b][1,5]oxazocine (Compound of -Reference Example 19; 88.5 mg) was reacted with 1-acetylpiperazine (48.1 mg) to obtain 9-(4-acetylpiperazine-1-yl)-5-[3,5-bis(trifluoromethyl)benzyl]-7-(2-methoxyphenyl)-6-oxo-2,3,4,5-tetrahydro-6H-pyrimido[4,5-b][1,5]oxazocine (86.2 mg, 90%).

MS(EI)m/z: 637(M$^+$) HRMS(EI): Calcd for $C_{30}H_{29}F_6N_5O_4$: 637.2124; found: 637.2085.

Example 30

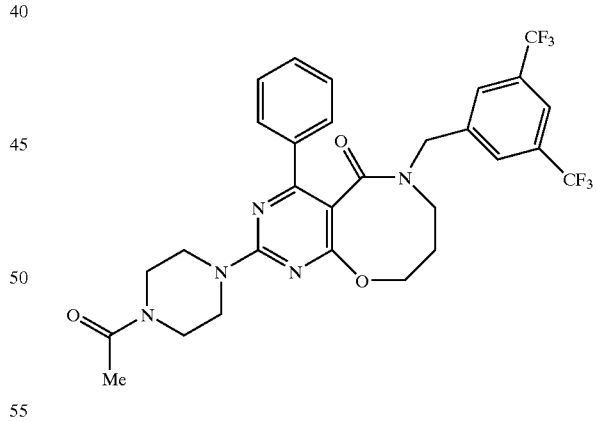

In a similar manner to Example 13, 5-[3,5-bis(trifluoromethyl)benzyl]-9-(methylsulfonyl)-6-oxo-7-phenyl-2,3,4,5-tetrahydro-6H-pyrimido[4,5-b][1,5]oxazocine (Compound of Reference Example 21; 84.0 mg) was reacted with 1-acetylpiperazine (23.1 mg) to obtain 9-(4-acetylpiperazine-1-yl)-5-[3,5-bis(trifluoromethyl)benzyl]-6-oxo-7-phenyl-2,3,4,5-tetrahydro-6H-pyrimido[4,5-b][1,5]oxazocine (53.7 mg, 59%).

MS(EI)m/z: 607(M$^+$) HRMS(EI): Calcd for $C_{29}H_{27}F_6N_5O_3$: 607.2018; found: 607.2049.

Example 31

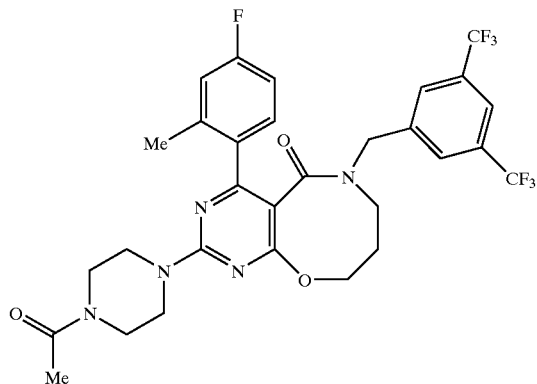

In a similar manner to Example 13, 5-[3,5-bis(trifluoromethyl)benzyl]-7-(4-fluoro-2-methylphenyl)- 9-(methylsulfonyl)-6-oxo-2,3,4,5-tetrahydro-6H-pyrimido[4,5-b][1,5]oxazocine (Compound of Reference Example 20; 88.8 mg) was reacted with 1-acetylpiperazine (23.1 mg) to obtain 9-(4-acetylpiperazine-1-yl)-5-[3,5-bis(trifluoromethyl)benzyl]-7-(4-fluoro-2-methylphenyl)-6-oxo-2,3,4,5-tetrahydro-6H-pyrimido[4,5-b][1,5]oxazocine (47.4 mg, 49%).

MS(EI)m/z: 639(M$^+$) HRMS(EI): Calcd for $C_{30}H_{28}F_7N_5O_3$: 639.2080; found: 639.2078.

Example 32

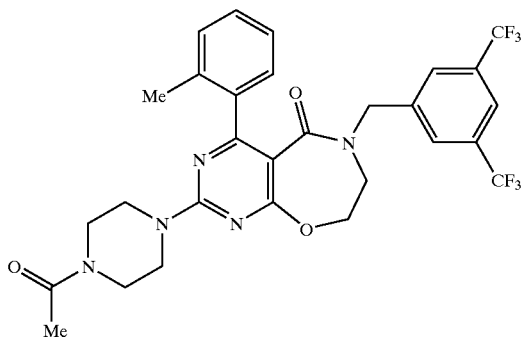

In a similar manner to Example 13, 4-[3,5-bis(trifluoromethyl)benzyl]-6-(2-methylphenyl)-8-(methylsulfonyl)-5-oxo-2,3,4,5-tetrahydropyrimido[5,4-f][1,4]oxazepine (Compound of Reference Example 22; 84.0 mg) was reacted with 1-acetylpiperazine (23.1 mg) to obtain 8-(4-acetylpiperazine-1-yl)-4-[3,5-bis(trifluoromethyl)benzyl]-6-(2-methylphenyl)-5-oxo-2,3,4,5-tetrahydropyrimido[5,4-f][1,4]oxazepine (62.2 mg, 68%).

MS(EI)m/z: 607(M$^+$) HRMS(EI): Calcd for $C_{29}H_{27}F_6N_5O_3$: 607.2018; found: 607.2026.

Example 33

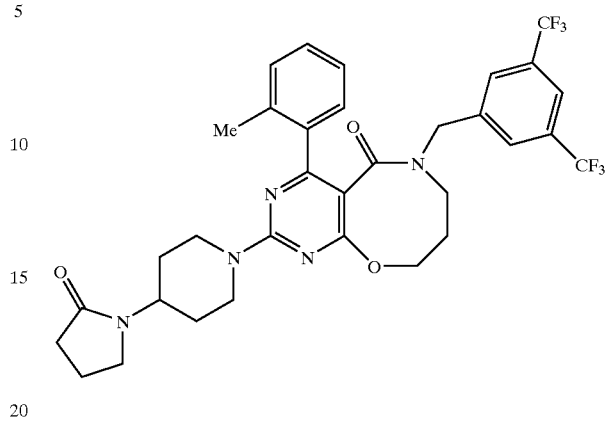

In a similar manner to Example 13, 5-[3,5-bis(trifluoromethyl)benzyl]-7-(2-methylphenyl)-9-(methylsulfonyl)-6-oxo-2,3,4,5-tetrahydro-6H-pyrimido[4,5-b][1,5]oxazocine (Compound of Reference Example 18; 86.1 mg) was reacted with 4-(2-oxopyrrolidine-1-yl)piperidine (30.3 mg) to obtain 5-[3,5-bis(trifluoromethyl)benzyl]-7-(2-methylphenyl)-6-oxo-9-[4-(2-oxopyrrolidine-1-yl)piperidine-1-yl]-2,3,4,5-tetrahydro-6H-pyrimido[4,5-b][1,5]oxazocine (80.8 mg, 81%).

MS(EI)m/z: 661(M$^+$) HRMS(EI): Calcd for $C_{33}H_{33}F_6N_5O_3$: 661.2488; found: 661.2512.

Example 34

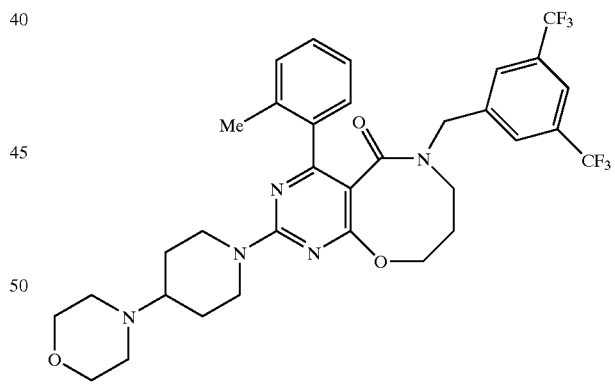

In a similar manner to Example 13, 5-[3,5-bis(trifluoromethyl)benzyl]-7-(2-methylphenyl)-9-(methylsulfonyl)-6-oxo-2,3,4,5-tetrahydro-6H-pyrimido[4,5-b][1,5]oxazocine (Compound of Reference Example 18; 86.1 mg) was reacted with 4-(morpholine-4-yl)piperidine (30.6 mg) to obtain 5-[3,5-bis(trifluoromethyl)benzyl]-7-(2-methylphenyl)-9-[4-(morpholine-4-yl)piperidine-1-yl]-6-oxo-2,3,4,5-tetrahydro-6H-pyrimido[4,5-b][1,5]oxazocine (72.6 mg, 73%).

MS(EI)m/z: 663(M$^+$) HRMS(EI): Calcd for $C_{33}H_{35}F_6N_5O_3$: 663.2644; found: 663.2654.

Example 35

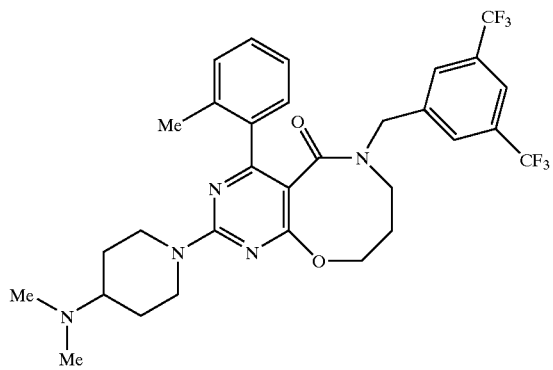

In a similar manner to Example 13, 5-[3,5-bis(trifluoromethyl)benzyl]-7-(2-methylphenyl)-9-(methylsulfonyl)-6-oxo-2,3,4,5-tetrahydro-6H-pyrimido[4,5-b][1,5]oxazocine (Compound of Reference Example 18; 86.1 mg) was reacted with 4-(dimethylamino)piperidine (23.1 mg) to obtain 5-[3,5-bis(trifluoromethyl)benzyl]-9-[4-(dimethylamino)piperidine-1-yl]-7-(2-methylphenyl)-6-oxo-2,3,4,5-tetrahydro-6H-pyrimido[4,5-b][1,5]oxazocine (84.2 mg, 90%).

MS(EI)m/z: 621(M$^+$) HRMS(EI): Calcd for $C_{31}H_{33}F_6N_5O_2$: 621.2538; found: 621.2524.

Example 36

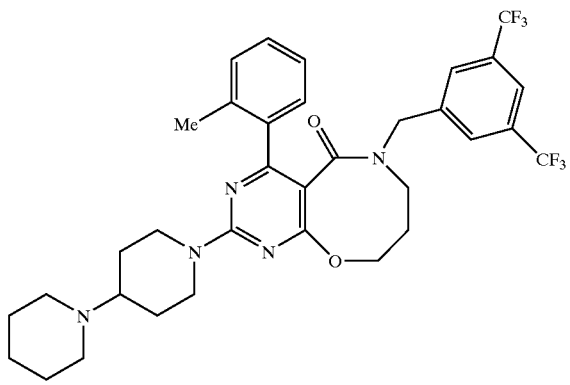

In a similar manner to Example 13, 5-[3,5-bis(trifluoromethyl)benzyl]-7-(2-methylphenyl)-9-(methylsulfonyl)-6-oxo-2,3,4,5-tetrahydro-6H-pyrimido[4,5-b][1,5]oxazocine (Compound of Reference Example 18; 86.1 mg) was reacted with 4-(piperidine-1-yl)piperidine (30.3 mg) to obtain 5-[3,5-bis(trifluoromethyl)benzyl]-7-(2-methylphenyl)-6-oxo-9-[4-(piperidine-1-yl)piperidine-1-yl]-2,3,4,5-tetrahydro-6H-pyrimido[4,5-b][1,5]oxazocine (86.7 mg, 87%).

MS(EI)m/z: 661(M$^+$) HRMS(EI): Calcd for $C_{34}H_{37}F_6N_5O_2$: 661.2851; found: 661.2845.

Example 37

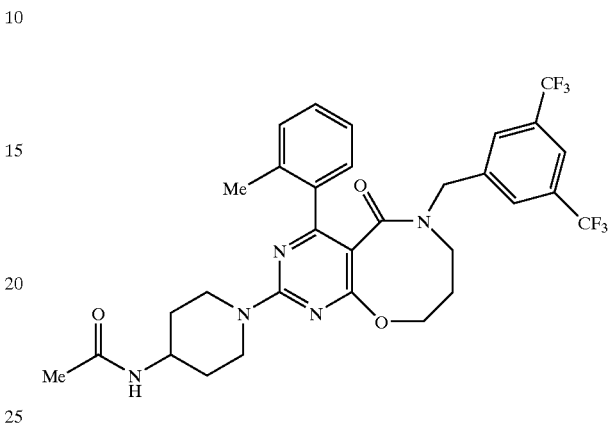

A mixture of 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg), 4-(t-butoxycarbonylamino)piperidine (36.1 mg), and 1,4-dioxane(1 mL) was refluxed for 5 hours while heated. The reaction mixture was diluted with ethyl acetate, was washed with water, and was dried over anhydrous sodium sulfate. The solvent was then removed to obtain a residue. While this residue was chilled on an ice bath, 3 mol/L hydrogen chloride-ethyl acetate (1 mL) was added and the mixture was stirred for 30 min. and then another hour at room temperature. The solvent was removed and the remaining product was dissolved in tetrahydrofuran (1 mL). While the solution was chilled on an ice bath, triethylamine (0.1 mL) and acetic anhydride (0.05 mL) were added and the resulting mixture was stirred at room temperature for 30 min. The reaction mixture was then diluted with ethyl acetate, was washed with water, and was then dried over anhydrous sodium sulfate. The solvent was removed and the resulting residue was purified on a silica gel column chromatography (ethyl acetate) to obtain 9-[4-(acetylamino)piperidine-1-yl]-5-[3,5-bis(trifluoromethyl)benzyl]-7-(2-methylphenyl)-6-oxo-2,3,4,5-tetrahydro-6H-pyrimido[4,5-b][1,5]oxazocine (51.0 mg, 53%).

MS(EI)m/z: 635(M$^+$) HRMS(EI): Calcd for $C_{31}H_{31}F_6N_5O_3$: 635.2331; found: 635.2360. $^1$H-NMR(400 Mz, CDCl$_3$)ppm: 1.25–1.41(2H, m), 1.91–2.05(6H, m), 2.07–2.19(1H, m), 2.25(3H, s), 3.04(2H, dd, J=11.2 and 11.2 Hz), 3.28(1H, dd, J=14.6 and 4.9 Hz), 3.75–3.90(1H, m), 3.85(1H, d, J=14.6 Hz), 3.99–4.09(1H, m), 4.28–4.42(2H, m), 4.72(2H, brd, J=12.7 Hz), 5.28–5.36(1H, m), 5.32(1H, d, J=14.6 Hz), 6.91–6.98(1H, m), 7.02–7.08(1H, m), 7.19–7.26(2H, m), 7.57(2H, s), 7.80(1H, s)

Example 38

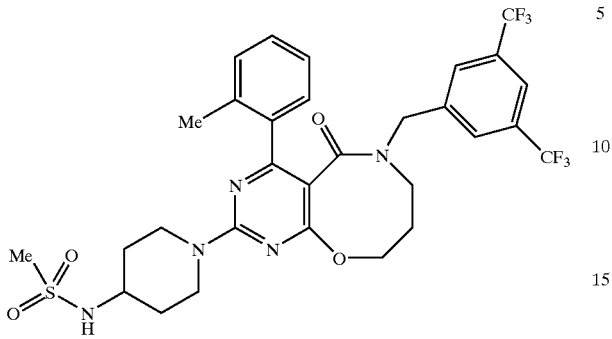

In a similar manner to Example 37, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg), 4-(t-butoxycarbonylamino)piperidine (36.1 mg), and methylsulfonylchloride (0.05 mL) were reacted to obtain 5-[3,5-bis(trifluoromethyl)benzyl]-9-[4-(methylsulfonylamino)piperidine-1-yl]-7-(2-methylphenyl)-6-oxo-2,3,4,5-tetrahydro-6H-pyrimido[4,5-b][1,5]oxazocine (31.7 mg, 31%).

MS(EI)m/z: 671(M$^+$) HRMS(EI): Calcd for $C_{30}H_{31}F_6N_5O_4S$: 671.2001; found: 671.2004. $^1$H-NMR(400 Mz, CDCl$_3$)ppm:1.42–1.54(2H, m), 1.91–2.19(5H, m), 2.25 (3H, s), 3.00(3H, s), 3.03–3.14(2H, m), 3.25–3.33(1H, m), 3.53–3.65(1H, m), 3.75–3.88(1H, m), 3.85(1H, d, J=14.6 Hz), 4.29–4.42(2H, m), 4.64–4.75(2H, m), 5.32(1H, d, J=14.6 Hz), 6.92–6.98(1H, m), 7.02–7.08(1H, m), 7.19–7.25 (2H, m), 7.57(2H, s), 7.80(1H, s)

Example 39

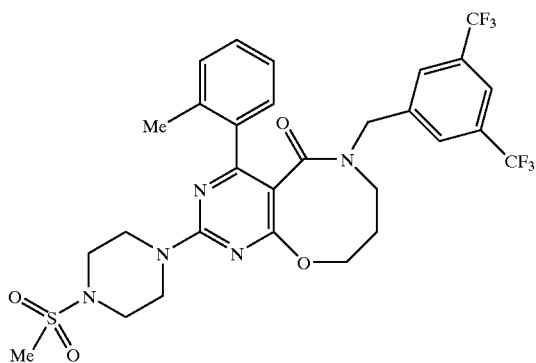

In a similar manner to Example 37, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg), 1-(t-butoxycarbonyl)piperazine (33.6 mg), and methylsulfonylchloride (0.05 mL) were reacted to obtain 5-[3,5-bis(trifluoromethyl)benzyl]-9-[4-(methylsulfonyl)piperazine-1-yl]-7-(2-methylphenyl)-6-oxo-2,3,4,5-tetrahydro-6H-pyrimido[4,5-b][1,5]oxazocine (54.6 mg, 55%).

MS(EI)m/z: 657(M$^+$) HRMS(EI): Calcd for $C_{29}H_{29}F_6N_5O_4S$: 657.1844; found: 657.1843.

Example 40

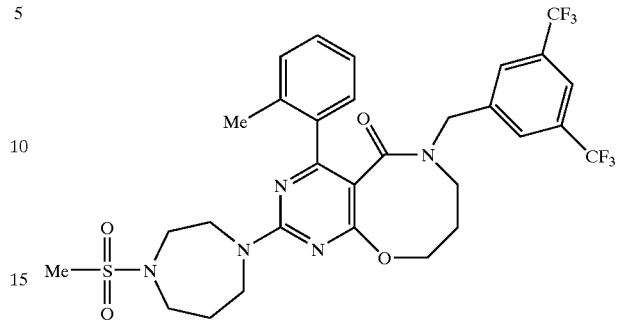

In a similar manner to Example 37, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg), 1-(t-butoxycarbonyl)homopiperazine (36.1 mg), and methylsulfonylchloride (0.05 mL) were reacted to obtain 5-[3,5-bis(trifluoromethyl)benzyl]-9-[4-(methylsulfonyl)homopiperazine-1-yl]-7-(2-methylphenyl)-6-oxo-2,3,4,5-tetrahydro-6H-pyrimido[4,5-b][1,5]oxazocine (46.4 mg, 46%).

MS(EI)m/z: 671(M$^+$) HRMS(EI): Calcd for $C_{30}H_{31}F_6N_5O_4S$: 671.2001; found: 671.2030.

Example 41

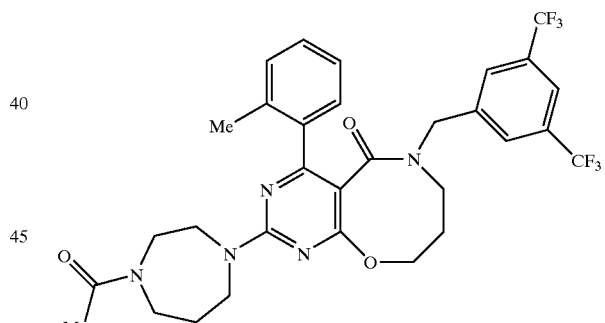

In a similar manner to Example 37, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg), 1-(t-butoxycarbonyl)homopiperazine (36.1 mg), and acetic anhydride (0.05 mL) were reacted to obtain 9-(4-acetylhomopiperazine-1-yl)-5-[3,5-bis(trifluoromethyl)benzyl]-7-(2-methylphenyl)-6-oxo-2,3,4,5-tetrahydro-6H-pyrimido[4,5-b][1,5]oxazocine (39.5 mg, 41%).

MS(EI)m/z: 635(M$^+$) HRMS(EI): Calcd for $C_{31}H_{31}F_6N_5O_3$: 635.2331; found: 635.2313. $^1$H-NMR(400 Mz, CDCl$_3$)ppm:1.83–2.06(4H, m), 2.12(3H, s), 2.25(3H, d, J=3.9 Hz), 3.29(1H, dd, J=15.1 and 4.4 Hz), 3.33–4.15(10H, m), 4.29–4.42(2H, m), 5.31(1H, d, J=15.1 Hz), 6.91–6.98 (1H, m), 7.01–7.08(1H, m), 7.19–7.25(2H, m), 7.57(2H, s), 7.80(1H, s)

Example 42

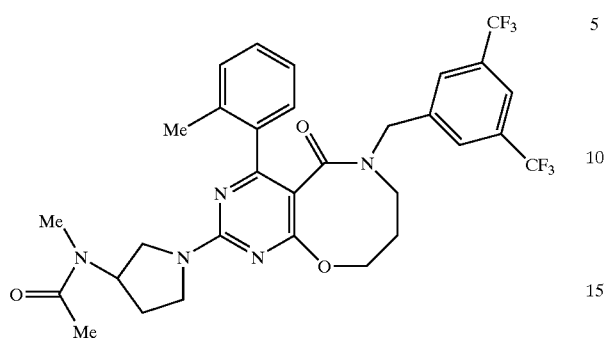

In a similar manner to Example 37, 5-[3,5-bis(trifluoromethyl)benzyl]-9-(methylsulfonyl)-7-(2-methylphenyl)-6-oxo-2,3,4,5-tetrahydro-6H-pyrimido[4,5-b][1,5]oxazocine (Compound of Reference Example 18; 86.0 mg), 3-(t-butoxycarbonylamino)-3-methylpyrrolidine (36.1 mg), and acetic anhydride (0.05 mL) were reacted to obtain 9-[3-(acetylamino)-3-methylpyrrolidine-1-yl]-5-[3,5-bis(trifluoromethyl)benzyl]-7-(2-methylphenyl)-6-oxo-2,3,4,5-tetrahydro-6H-pyrimido[4,5-b][1,5]oxazocine (52.9 mg, 56%).

MS(EI)m/z: 635(M$^+$) HRMS(EI): Calcd for $C_{31}H_{31}F_6N_5O_3$: 635.2331; found: 635.2293.

Example 43

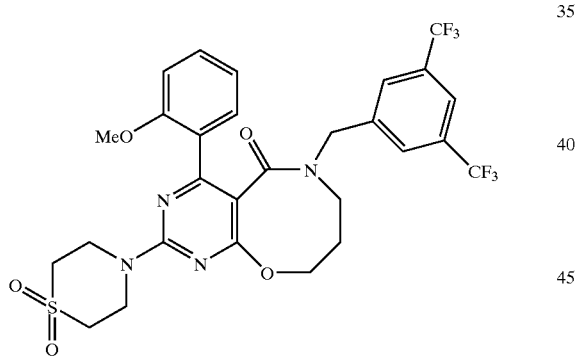

A mixture of 5-[3,5-bis(trifluoromethyl)benzyl]-9-(methylsulfonyl)-7-(2-methoxyphenyl)-6-oxo-2,3,4,5-tetrahydro-6H-pyrimido[4,5-b][1,5]oxazocine (Compound of Reference Example 19; 118 mg), thiomorpholine (100 mg), and 1,4-dioxane (1 mL) was refluxed for 5 hours while heated. The reaction mixture was diluted with ethyl acetate, was washed with water, and was then dried over anhydrous sodium sulfate. The solvent was removed and the resulting residue was purified on a silica gel column chromatography (hexane:ethyl acetate=10:1). The resultant crystal was dissolved in tetrahydrofuran (1 mL), followed by addition of 3-chloroperbenzoic acid (105 mg) and stirring for 3 hours at room temperature. Subsequently, the reaction mixture was diluted with ethyl acetate, was washed with a saturated aqueous solution of sodium hydrogen carbonate, and was then dried over anhydrous sodium sulfate. The solvent was removed and the resulting residue was purified on a silica gel column chromatography (hexane:ethyl acetate=2:1) to obtain 5-[3,5-bis(trifluoromethyl)benzyl]-9-(1,1-dioxothiomorpholine-4-yl)-7-(2-methoxyphenyl)-6-oxo-2,3,4,5-tetrahydro-6H-pyrimido[4,5-b][1,5]oxazocine (104 mg, 81%).

MS(EI)m/z: 644(M$^+$) HRMS(EI): Calcd for $C_{28}H_{26}F_6N_4O_5S$: 644.1528; found: 644.1555.

Example 44

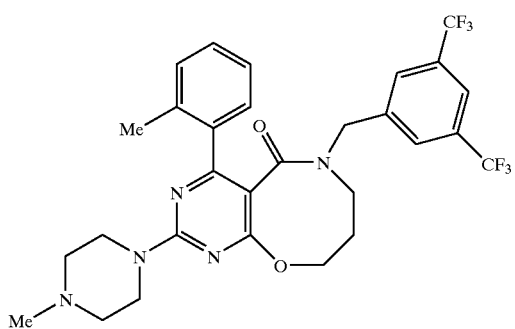

In a similar manner to Example 13, 5-[3,5-bis(trifluoromethyl)benzyl]-7-(2-methylphenyl)-9-(methylsulfonyl)-6-oxo-2,3,4,5-tetrahydro-6H-pyrimido[4,5-b][1,5]oxazocine (Compound of Reference Example 18; 115 mg) was reacted with 1-methylpiperazine (40.3 mg) to obtain 5-[3,5-bis(trifluoromethyl)benzyl]-7-(2-methylphenyl)-9-(4-methylpiperazine-1-yl)-6-oxo-2,3,4,5-tetrahydro-6H-pyrimido[4,5-b][1,5]oxazocine (76.2 mg, 61%).

MS(FAB$^+$) m/z: 594 (M+H$^+$) HRMS(FAB$^+$): Calcd for $C_{29}H_{30}F_6N_5O_2$: 594.2304; found: 594.2289.

Example 45

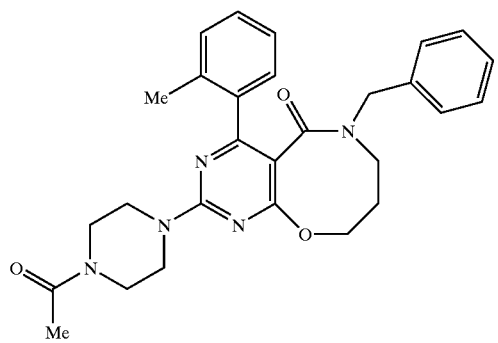

In a similar manner to Example 13, 5-benzyl-7-(2-methylphenyl)-9-(methylsulfonyl)-6-oxo-2,3,4,5-tetrahydro-6H-pyrimido[4,5-b][1,5]oxazocine (Compound of Reference Example 32; 65.7 mg) was reacted with 1-acetylpiperazine (23.1 mg) to obtain 9-(4-acetylpiperazine-1-yl)-5-benzyl-7-(2-methylphenyl)-6-oxo-2,3,4,5-tetrahydro-6H-pyrimido[4,5-b][1,5]oxazocine (45.0 mg, 62%).

MS(FAB$^+$) m/z: 486 (M+H$^+$) HRMS(FAB$^+$): Calcd for $C_{28}H_{32}N_5O_3$: 486.2505; found: 486.2505.

Example 46

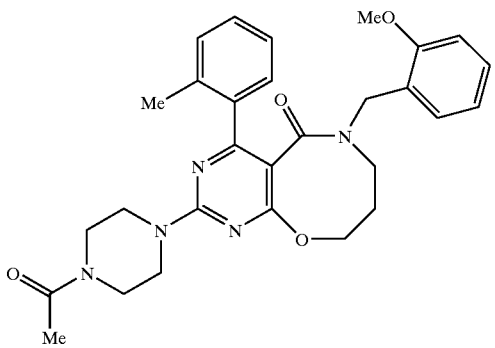

In a similar manner to Example 13, 5-(2-methoxybenzyl)-7-(2-methylphenyl)-9-(methylsulfonyl)-6-oxo-2,3,4,5-tetrahydro-6H-pyrimido[4,5-b][1,5]oxazocine (Compound of Reference Example 33; 70.2 mg) was reacted with 1-acetylpiperazine (23.1 mg) to obtain 9-(4-acetylpiperazine-1-yl)-5-(2-methoxybenzyl)-7-(2-methylphenyl)-6-oxo-2,3,4,5-tetrahydro-6H-pyrimido[4,5-b][1,5]oxazocine (48.3 mg, 62%).

MS(FAB$^+$) m/z: 516 (M+H$^+$) HRMS(FAB$^+$): Calcd for $C_{29}H_{34}N_5O_4$: 516.2611; found: 516.2610.

Example 47

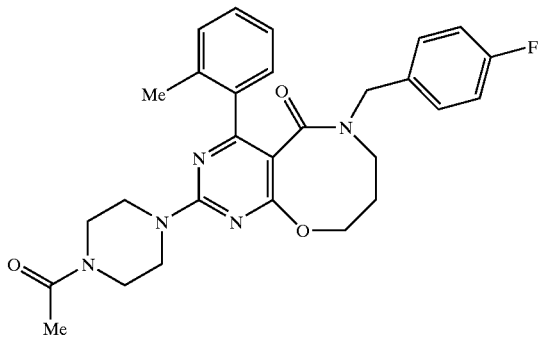

In a similar manner to Example 13, 5-(4-fluorobenzyl)-7-(2-methylphenyl)-9-(methylsulfonyl)-6-oxo-2,3,4,5-tetrahydro-6H-pyrimido[4,5-b][1,5]oxazocine (Compound of Reference Example 34; 68.4 mg) was reacted with 1-acetylpiperazine (23.1 mg) to obtain 9-(4-acetylpiperazine-1-yl)-5-(4-fluorobenzyl)-7-(2-methylphenyl)-6-oxo-2,3,4,5-tetrahydro-6H-pyrimido[4,5-b][1,5]oxazocine (42.0 mg, 55%).

MS(FAB$^+$) m/z: 504 (M+H$^+$) HRMS(FAB$^+$): Calcd for $C_{28}H_{31}FN_5O_3$: 504.2411; found: 504.2408.

Evidence of the effectiveness of the compounds of the present invention is provided below with reference to Test Examples.

Test Examples (1) Test for NK1 Receptor Antagonist

The method used was according to the method proposed by S. Dion et al.(Dion et al., *Life Sciences* 41(1987): 2269), to which minor modifications were made.

Guinea pigs were stunned by a blow on the head and were exsanguinated from the carotid artery and ilea were isolated. The ileum was mounted in an organ bath containing Tyrode's solution which was maintained at 32° C., and gased with 95% $O_2$ and 5% $CO_2$. The ileum was subjected to a resting tension of 1-gram and allowed to equilibrate for 20 minutes before the experiment was started. As a control, a concentration-response curve for substance P in the absence of any of test compounds was used. The NK1 receptor antagonist activity of each test compound was determined by a concentration-response curve obtained by pretreating at least three concentrations of the test compound for 10 minutes and subsequently applying substance P in a cumulative manner. The Kb values were determined according to the method of Schild and the results are shown in Table 1 (Schild *Brit. J. Pharmacol.* 14(1959): 49).

The composition of the Tyrode's solution was as follows: NaCl=136.9, KCl=2.7, $CaCl_2.2H_2O$=2.5, $MgCl_2.6H_2O$=1.0, $NaH_2PO_4.2H_2O$=0.4, $NaHCO_3$=11.9, glucose=11.1(mmol/L)

TABLE 1

| Test Compounds | Kb(nmol/L) |
| --- | --- |
| Compound of Example 2 | 0.294 |
| Compound of Example 13 | 0.217 |
| Compound of Example 14 | 0.798 |
| Compound of Example 16 | 0.105 |
| Compound of Example 18 | 0.459 |
| Compound of Example 20 | 0.0794 |
| Compound of Example 25 | 0.427 |
| Compound of Example 26 | 0.398 |
| Compound of Example 27 | 0.440 |
| Compound of Example 29 | 0.100 |
| Compound of Example 37 | 0.151 |
| Compound of Example 38 | 0.214 |
| Compound of Example 41 | 0.308 |
| Compound of Example 43 | 0.123 |
| Compound of Example 44 | 0.00631 |
| TAK-637* | 0.269 |

*Compound described in Example 18 in Japanese Patent Laid-Open Publication No. Hei 9-263585

As can be seen from the results of Table 1, the compounds (1) or salts thereof prove to be effective NK1 receptor antagonists.

(2) Cystometry Test on Guinea Pigs

The method used was according to the method proposed by J S. Peterson et al. (Peterson J S. et al., *J. Pharmacol. Methods* 21(1989): 231), to which minor modifications were made.

Guinea pigs were anesthetized with halothane and the tenth thoracic spinal cord was cut in each animal. Subsequently, both ureters were ligated and were cut on the kidney-side. Polyethylene catheters were inserted into the bladder to provide an injection pathway for physiological saline and a pathway for the measurement of intravesical pressure. Each animal was restricted in a Ballman cage and was left for more than 2 hours. Subsequently, room-temperature saline was injected through the bladder catheter into the bladder at a rate of 6 mL/hr to conduct a cystometry test. Once the effective bladder capacity was stabilized, a test compound was intravenously administered into the jugular vein. The effective bladder capacity is defined as the volume of saline injected from one urination to the next. The effect of each test compound was determined as the increase in the average bladder volume, which was determined based on the average bladder volume measured 30 minutes prior to the administration of the test compound and the average bladder volume measured every 30 minutes after the administration of the test compound. The results are shown in Table 2.

TABLE 2

| Test compounds | Dose (i.v.) mg/kg | Increase in bladder capacity (%) |
|---|---|---|
| Compound of Example 16 | 0.3 | 59.4 |
| Compound of Example 20 | 0.3 | 40.4 |
| Compound of Example 41 | 0.3 | 36.8 |
| TAK-637* | 0.3 | 12.0 |
|  | 1 | 23.8 |
|  | 3 | 20.5 |

*Compound described in Example 18 in Japanese Patent Laid-Open Publication No. Hei 9-263585

As can be inferred from the results of Table 2, the compounds (1) or salts thereof have a better ability to increase the effective bladder capacity than TAK-637 in terms of the potency as well as the maximum effects.

INDUSTRIAL APPLICABILITY

As set forth, the present invention has been devised based on the discovery that the novel fused bicyclic pyrimidine derivatives and salts thereof act as effective tachykinin receptor antagonists.

In particular, not only have the compounds of the present invention proven to act as NK1 receptor antagonists, but they have also been shown, by the Test Examples above, to have better effects than the conventional compounds.

Specifically, the compounds of the present invention proved to exhibit significantly higher pharmacological effects as compared to TAK-637, a known compound, when tested for their effects on dysuria, a tachykinin-mediated disorder, by cystometry, during which the ability of each of the compounds to increase the effective bladder capacity was determined in guinea pigs with broken spinal cords. In brief, when given in smaller doses, the compounds of the present invention exhibited pharmacological effects comparable to the conventional TAK-637 compound. Also, the same doses of the compounds of the present invention brought about significantly better pharmacological effects and elicited higher maximum effects than TAK-637.

In addition, the compounds of the present invention and salts thereof exhibit little toxicity and are thus proven to be highly safe. Accordingly, the compounds of the present invention and salts thereof, which are effective tachykinin antagonists, are of significant usefulness in the treatment of various pathological conditions including pollakiuria.

What is claimed is:

1. A compound of formula (1), or a salt thereof:

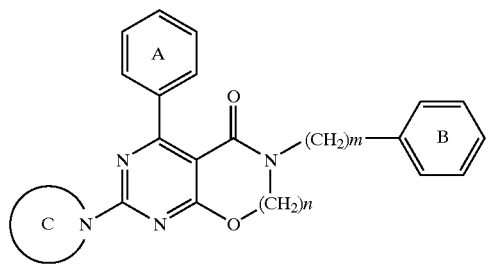

(1)

wherein the rings A and B are each a benzene ring, which may have 1 to 3 substituents (any adjacent two of which may be bound to one another to form a ring selected from the group consisting of

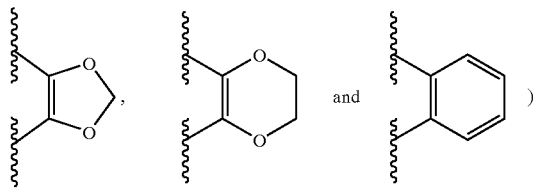

)

that are each independently selected from the group consisting of a halogen atom, a $C_1$ to $C_6$ alkyl group, which may be substituted with a halogen atom, and a $C_1$ to $C_6$ alkoxyl group;

the ring C is a 5- to 7-membered nitrogen-containing ring, which may contain, aside from the nitrogen atom, 1 to 3 heteroatoms selected from the group consisting of a nitrogen atom, a sulfur atom, and an oxygen atom;

the ring C may further contain a substituent selected from the group consisting of a $C_1$ to $C_6$ alkyl group, a hydroxyl group, a $C_1$ to $C_6$ alkoxyl group, a formyl group, a $C_1$ to $C_6$ alkylcarbonyl group, a $C_1$ to $C_6$ alkoxycarbonyl group, a carbamoyl group, a mono- or di-substituted $C_1$ to $C_6$ alkylcarbamoyl group, a $C_1$ to $C_6$ alkylsulfonyl group, an amino group, a mono- or di-substituted $C_1$ to $C_6$ alkylamino group, a $C_1$ to $C_6$ alkylcarbonylamino group, a $C_1$ to $C_6$ alkoxycarbonylamino group, a $C_1$ to $C_6$ alkylsulfonylamino group, an oxo group, a 6-membered aromatic heterocyclic group, and a substituent represented by the following formula:

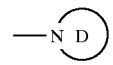

wherein the ring D is a 3- to 7-membered nonaromatic heterocyclic ring, which may contain, aside from the nitrogen atom, 1 to 3 heteroatoms selected from the group consisting of a nitrogen atom, a sulfur atom, and an oxygen atom and may further contain 1 or 2 oxo-substituted carbon atoms;

m is 1 or 2; and n is 2 or 3.

2. The compound according to claim 1 represented by formula (1a), or a salt thereof:

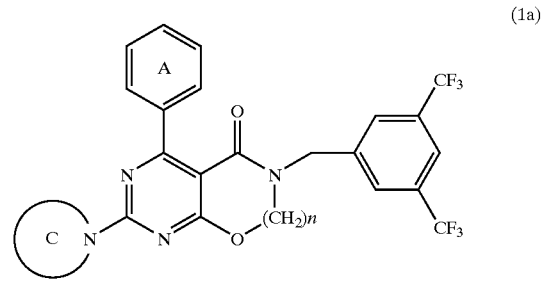

(1a)

wherein the ring A is a benzene ring, which may have 1 to 3 substituents (any adjacent two of which may be bound to one another to form a ring) that are each independently selected from the group consisting of a halogen atom, a $C_1$ to $C_6$ alkyl group, which may be substituted with a halogen atom, and a $C_1$ to $C_6$ alkoxyl group;

the ring C is a 5- to 7-membered nitrogen-containing ring, which may contain, aside from the nitrogen atom, 1 to 3 heteroatoms selected from the group consisting of a nitrogen atom, a sulfur atom, and an oxygen atom;

the ring C may further contain a substituent selected from the group consisting of a $C_1$ to $C_6$ alkyl group, a hydroxyl group, a $C_1$ to $C_6$ alkoxyl group, a formyl group, a $C_1$ to $C_6$ alkylcarbonyl group, a $C_1$ to $C_6$ alkoxycarbonyl group, a carbamoyl group, a mono- or di-substituted $C_1$ to $C_6$ alkylcarbamoyl group, a $C_1$ to $C_6$ alkylsulfonyl group, an amino group, a mono- or di-substituted $C_1$ to $C_6$ alkylamino group, a $C_1$ to $C_6$ alkylcarbonylamino group, a $C_1$ to $C_6$ alkoxycarbonylamino group, a $C_1$ to $C_6$ alkylsulfonylamino group, an oxo group, a 6-membered aromatic heterocyclic group, and a substituent represented by the following formula:

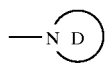

wherein the ring D is a 3- to 7-membered nonaromatic heterocyclic ring, which may contain, aside from the nitrogen atom, 1 to 3 heteroatoms selected from the group consisting of a nitrogen atom, a sulfur atom, and an oxygen atom and may further contain 1 or 2 oxo-substituted carbon atoms; and n is 2 or 3.

3. The compound according to claim 2, or a salt thereof, wherein in the formula (1a), the ring C is represented either by the following formula:

wherein $R^1$ is a hydroxyl group, a C1 to C6 alkoxy group, a formyl group, a C1 to C6 alkylcarbonyl group, a C1 to C6 alkoxycarbonyl group, a carbamoyl group, a mono- or di-substituted C1 to C6 alkylcarbamoyl group, an amino group, a mono- or di-substituted C1 to C6 alkylamino group, a C1 to C6 alkylcarbonylamino group, a C1 to C6 alkoxycarbonylamino group, a C1 to C6 alkylsulfonylamino group, an oxo group, a 6-membered aromatic heterocyclic group, or a substituent represented by the following formula:

wherein the ring D is a 3- to 7-membered nonaromatic heterocyclic ring, which may contain, aside from the nitrogen atom, 1 to 3 heteroatoms selected from the group consisting of a nitrogen atom, a sulfur atom, and an oxygen atom and may further contain 1 or 2 oxo-substituted carbon atoms.

4. The compound according to claim 2, or a salt thereof, wherein in the formula (1a), the ring C is represented by the following formula:

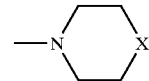

wherein X is —O— or —S(O)$_q$—; and q is 0, 1, or 2.

5. The compound according to claim 2, or a salt thereof, wherein in the formula (1a), the ring C is a functional group represented by the following formula:

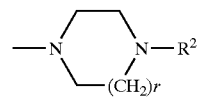

wherein $R^2$ is a hydrogen atom, a $C_1$ to $C_6$ alkyl group, a formyl group, a $C_1$ to $C_6$ alkylcarbonyl group, a $C_1$ to $C_6$ alkoxycarbonyl group, a carbamoyl group, a mono- or di-substituted $C_1$ to $C_6$ alkylcarbamoyl group or a $C_1$ to $C_6$ alkylsulfonyl group; and r is 1 or 2.

6. The compound according to claim 2, or a salt thereof, wherein in the formula (1a), the ring C is represented by the following formula:

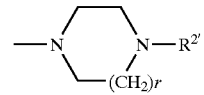

wherein $R^{2'}$ is an acetyl group or a methylsulfonyl group; and r is 1 or 2.

7. The compound according to claim 2, or a salt thereof, wherein the ring C in the formula (1a) is represented by the following formula:

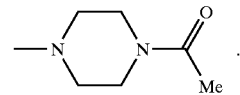

8. The compound according to claim 7, or a salt thereof, wherein in the formula (1a), n is 3.

9. The compound according to claim 1, wherein the compound represented by the formula (1) is 9-(4-acetylpiperazine-1-yl)-5-[3,5-bis(trifluoromethyl)benzyl]-7-(2-methylphenyl)-6-oxo-2,3,4,5-tetrahydro-6H-pyrimido[4,5-b][1,5]oxazocine.

10. The compound according to claim 1, wherein the compound represented by the formula (1) is 5-[3,5-bis(trifluoromethyl)benzyl]-9-(1,1-dioxothiomorpholine-4-yl)-7-(2-methylphenyl)-6-oxo-2,3,4,5-tetrahydro-6H-pyrimido[4,5-b][1,5]oxazocine.

11. The compound according to claim 1, wherein the compound represented by the formula (1) is 9-(4-acetylhomopiperazine-1-yl)-5-[3,5-bis(trifluoromethyl)benzyl]-7-(2-methylphenyl)-6-oxo-2,3,4,5-tetrahydro-6H-pyrimido[4,5-b][1,5]oxazocine.

12. The compound according to claim 1, wherein the compound represented by the formula (1) is 5-[3,5-bis(trifluoromethyl)benzyl]-7-(2-methylphenyl)-9-(4-methylpiperazine-1-yl)-6-oxo-2,3,4,5-tetrahydro-6H-pyrimido[4,5-b][1,5]oxazocine.

13. A method of treating dysuria, which comprises administering a therapeutically effective amount of a compound according to claim 1, or a salt thereof to a patient in need thereof.

14. The method according to claim 13, wherein the dysuria is increased urinary frequency or incontinence of urine.

15. A pharmaceutical composition containing a compound according to claim 1 or a salt thereof as active ingredient, and one or more pharmaceutically acceptable adjuvants.

* * * * *